US008160819B2

(12) United States Patent
Fagerquist et al.

(10) Patent No.: US 8,160,819 B2
(45) Date of Patent: Apr. 17, 2012

(54) RAPID IDENTIFICATION OF PROTEINS AND THEIR CORRESPONDING SOURCE ORGANISMS BY GAS PHASE FRAGMENTATION AND IDENTIFICATION OF PROTEIN BIOMARKERS

(75) Inventors: Clifton K. Fagerquist, Brentwood, CA (US); Leslie A. Harden, Richmond, CA (US); Brandon R Garbus, Santa Clara, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 412 days.

(21) Appl. No.: 12/415,741

(22) Filed: Mar. 31, 2009

(65) Prior Publication Data

US 2010/0057372 A1 Mar. 4, 2010

Related U.S. Application Data

(60) Provisional application No. 61/191,609, filed on Sep. 9, 2008, provisional application No. 61/091,039, filed on Aug. 22, 2008.

(51) Int. Cl.
*G01N 33/68* (2006.01)
(52) U.S. Cl. .......................................... 702/20; 702/19
(58) Field of Classification Search ................... 702/19, 702/20, 27, 182; 250/281, 282; 435/6.14, 435/7.1; 436/86
See application file for complete search history.

(56) References Cited

U.S. PATENT DOCUMENTS

| 6,300,627 | B1 | 10/2001 | Koster et al. | |
|---|---|---|---|---|
| 6,393,367 | B1* | 5/2002 | Tang et al. | 702/19 |
| 6,446,010 | B1* | 9/2002 | Eriksson et al. | 702/19 |
| 7,020,559 | B1 | 3/2006 | Demirev et al. | |
| 2002/0152033 | A1* | 10/2002 | Beavis et al. | 702/19 |

OTHER PUBLICATIONS

Arnold, R.J. and J.P. Reilly, "Fingerprint Matching of *E. coli* Strains with Matrix-assisted Laser Desorption/Ionization Time-of-Flight Mass Spectrometry of Whole Cells Using a Modified Correlation Approach" Rapid Communications in Mass Spectrometry (1998) 12:630-636.
Balasundaram, B and A.B. Pandit, "Significance of Location of Enzymes on Their Release During Microbial Cell Disruption" Biotechnology and Bioengineering (2001) 75(5):607-614.
Beavis, R.C. and B.T. Chait, "Cinnamic Acid Derivatives as Matrices for Ultraviolet Laser Desorption Mass Spectrometry of Proteins" Rapid Communications in Mass Spectrometry (1989) 3(12):432-435.
Bhattacharya, S.H., T.J. Raiford, and K.K. Murray, "Infrared Laser Desorption/Ionization on Silicon" Anal. Chem. (2002) 74:2228-2231.

(Continued)

*Primary Examiner* — John H Le
(74) *Attorney, Agent, or Firm* — Elizabeth R. Sampson; Leslie Shaw; John Fado

(57) ABSTRACT

Embodiments of the present invention relate to the identification of proteins using laser desorption ionization mass spectrometry, the identification of source organisms from which the identified proteins are derived and a computer readable storage medium storing instructions that, when executed by a computer cause the computer to perform a method for the identification of proteins using mass spectra generated through the application of laser desorption ionization mass spectrometry of the proteins.

32 Claims, 13 Drawing Sheets

OTHER PUBLICATIONS

Cain, T.C., D.M. Lubman and W.J. Weber Jr., "Differentiation of Bacteria Using Protein Profiles from Matrix-assisted Laser Desorption/Ionization Time-of-Flight Mass Spectrometry" Rapid Comm. in Mass Spectrometry (1994) 8:1026-1030.

Dai, Y et al., "Detection and Indentification of Low-mass Peptides and Proteins from Solvent Suspensions of *Escherichia coli* by High Performance Liquid Chromatography Fractionation and Matrix-assisted Laser Desorption/ Ionization Mass Spectrometry" Rapid Comm. in Mass Spectromerty (1999) 13:73-78.

Demirev, P.A., et al. "Microorganism Identification by Mass Spectrometry and Protein Database Searches" Anal. Chem. (1999) 71:2732-2738.

Demirev, P.A. et al., "Bioinformatics and Mass Spectrometry for Microorganism Indentification: Proteome-Wide Post-Translational Modifications and Database Search Algroithms for Characterization of Intact *H. pylori*" Anal. Chem. (2001) 73:4566-4573.

Demirev, P.A. et al., "Top-Down Proteomics for Rapid Identification of Intact Microorganisms" Anal. Chem. (2005) 77:7455-7461.

Fagerquist, C.K. et al., "Genomic and Proteomic Identification of a DNA-Binding Protein Used in the "Fingerprinting" of Campylobacter Species and Strains by MALDI-TOF-MS Protein Biomarker Analysis" Anal. Chem. (2005) 77:4897-4907.

Fagerquist, C.K. et al. "Sub-Speciating *Campylobacter jejuni* by Proteomic Analysis of its Protein Biomarkers and Their Post-Translational Modifications" J. Proteome Res. (2006) 5:2527-2538.

Fagerquist, C.K., "Amino Acid Sequence Determination of Protein Biomarkers of *Campylobacter upsaliensis* and *C.helveticus* by "Composite" Sequence Proteomic Analysis" J. Proteome Res. (2007) 6:2539-2549.

Fenn, J.B. et al. "Electrospray Ionization for Mass Spectrometry of Large Biomolecules" Science (1989) 246:64-71.

Fenselau, C. and P.A. Demirev, "Characterization of Intact Microorganisms by Maldi Mass Spectrometry" Mass Spec. Rev. (2001) 20:157-171.

Gardy, J.L., and F.S.L. Brinkman, "Methods for predicting bacterial protein subcellular localization" (2006) . Microbiology 4:741-751.

Haag, A.M. et al., "Rapid Identification and Speciation of Haemophilus Bacteria by Matrix-assisted Laser Desorption/ Ionization Time-of-flight Mass Spectrometry" J. Mass Spec. (1998) 33:750-756.

Henzel, W.J. et al., "Identifying proteins from two-dimensional gels by molecular mass searching of peptide fragments in protein sequence databases" (1993) 90:5011-5015.

Holland, R.D. et al., "Rapid Identification of Intact Whole Bacteria Based on Spectral Patterns using Matrix-assisted Laser Desorption/Ionization with Time-of-flight Mass Spectrometry" Rapid Comm. in Mass Spec. (1996) 10:1227-1232.

James, P. et al. "Protein Identification by Mass Profile Fingerprinting" Biochem. and Biophys. Res. Comm. (1993) 195 (1):58-64.

Jarman, K.H. et al., "An Algorithm for Automated Bacterial Identification Using Matrix-Assisted Laser Desorption/ Ionization Mass Spectrometry" Anal. Chem. (2000) 72:1217-1223.

Karas, M. et al., "Matrix-Assisted Ultraviolet Laser Desorption of Non-Volatile Compounds" Int. J. Mass Spec. and Ion Proc. (1987) 78:53-68.

Karas, M. et al., "Laser Desorption Ionization of Proteins with Molecular Masses Exceeding 10 000 Daltons" Anal. Chem. (1988) 60:2299-2301.

Karas, M. and U. Bahr, "Laser desorption ionization mass spectrometry of large biomolecules" Trends in Analy. Chem. (1990) 9(10):321-325.

Krishnamurthy, T., P.L. Ross, and U. Rajamani, "Detection of Pathogenic and Non-pathogenic Bacteria by Matrix-assisted Laser Desorption/Ionization Time-of-flight Mass Spectrometry" Rapid Comm. in Mass Spec. (1996) 10:883-888.

Krishnamurthy, T. and P.L. Ross, "Rapid Identification of Bacteria by Direct Matrix-assisted Laser Desorption/Ionization Mass Spectrometric Analysis of Whole Cells" Rapid Comm. Mass Spec. (1996) 10:1992-1996.

Lancaster, K.S., H.J. An, B. Li, and C.B. Lebrilla, "Interrogation of N-Linked Oligosaccharides Using Infrared Multiphoton Dissociation in FT-ICR Mass Spectrometry" Anal. Chem. (2006) 78:4990-4997.

Lay, Jr. J.0. "MALDI-TOF Mass Spectrometry of Bacteria" Mass Spec. Rev. (2001) 20:172-194.

Lin, M. et al., "Intact protein analysis by matrix-assisted laser desorption/ionization tandem time-of-flight mass spectrometry" Rapid Comm. Mass Spec. (2003) 17:1809-1814.

Mandrell, R.E. et al., "Specation of *Campylobacter coli*, *C. jejuni*, *C. helveticus*, *C. lari*, *C. sputorum*, and *C. upsaliensis* by Matrix-Assisted Laser Desorption Ionization-Time of Flight Mass Spectrometry" Applied and Environ. Microbiol. (2005) 71:6292-6307.

Mann, M., P. Hojrup, and P. Roepstorff, "Use of Mass Spectrometric Molecular Weight Information to Identify Proteins in Sequence Databases" Biolog. Mass Spectrometry (1993) 22:338-345.

Mead, P.S. et al., "Food-Related Illness and Death in the United States" Emerging Infectious Diseases (1999) 5 (5):607-625.

Medzihradszky, K.F. et al., "The Characteristics of Peptide Collision-Induced Dissociation Using a High-Performance MALDI-TOF/TOF Tandem Mass Spectrometer" Anal. Chem. (2000) 72:552-558.

Meng, F. et al., "Informatics and multiplexing of intact protein identification in bacteria and the archaea" Nature Biotech. (2001) 19:952-957.

Mortz, E. et al., "Sequence tag identification of intact proteins by matching tandem mass spectral data against sequence data bases" Proc. Natl. Acad. Sci. (1996) 93:8264-8467.

Neidigh, J. W., R. M. Fesinmeyer, and N.H. Andersen, "Designing a 20-residue protein" Nature Structural Biology (2002) 9(6):425-430.

Onnerfjord, P. et al., "Homogeneous Sample Preparation for Automated High Throughput Analysis with Matrix-assisted Laser Desorption/Ionisation Time-of-flight Mass Spectrometry" Rap. Comm. Mass Spec. (1999) 13:315-322.

Pappin, D.J.C., P. Hojrup, and A.J. Bleasby, "Rapid identification of proteins by peptide-mass fingerprinting" Current Biology (1993) 3(6):327-332.

Perkins, D.N. et al., "Probability-based protein identification by searching sequence databases using mass spectrometry data" Electrophoresis (1999) 20:3551-3567.

Pineda, F.J. et al., "Testing the Significance of Microorganism Identification by Mass Spectrometry and Proteome Database Search" Anal. Chem. (2000) 72:3739-3744.

Pineda, F.J. et al., "Microorganism Identification by Matrix-Assisted Laser/Desorption Ionization Mass Spectrometry and Model-Derived Ribosomal Protein Biomarkers" Anal. Chem. (2003) 3817-3822.

Ragoussis, J. et al., "Matrix-Assisted Laser Desorption/Ionisation, Time-of-Flight Mass Spectrometry in Genomics Research" PLoS Genetics (2006) 2(7):920-929.

Ramirez, J. and C. Fenselau, "Factors contributing to peak broadening and mass accuracy in the characterization of intact spores using matrix-assisted laser desorption/ionization coupled with the time-of-flight mass spectrometry" J. Mass Spec. (2001) 36:929-936.

Santoni, V., M. Molloy, and T. Rabilloud, "Membrane proteins and proteomics: Un amour impossible?" Electrophoresis (2000) 21:1054-1070.

Smejkal, G.B. et al., "Increased Protein Yield from *Escherichia coli* Using Pressure-Cycling Technology" J. Biomolecular Tech. (2006) 17(2):173-175.

Strupat, K., M. Karas and F. Hillenkamp, "2,5-Dihydroxybenzoic acid: a new matrix for laser desorption-ionization mass spectrometry" Int. J. Mass Spec and Ion Proc. (1991) 111:89-102.

Tanaka, K. et al., "Detection of High Mass Molecules by Laser Desorption Time-of-Flight Mass Spectrometry" Proceeding of the 2nd Japan-China Joint Symposium on Mass Spec, Osaka, Japan (1987) 185-188.

Tang, N. et al., "Current Developments in Seldi Affinity Technology" Mass Spec. Rev. (2004) 23:34-44.

Taylor, J.A. and R.S. Johnson, "Implemenation and Uses of Automated de Novo Peptide Sequencing by Tandem Mass Spectrometry" Anal. Chem. (2001) 73:2594-2604.

Vaidyanathan, S. et al., "Laser desorption/ionization mass spectrometry on porous silicon for metabolome analyses:influence of surface oxidation" Rap. Comm. in Mass Spec. (2007) 21:2157-2166.

Wahl, K.L. et al., "Analysis of Microbial Mixtures by Matrix-Assited Laser Desorption/Ionization Time-of-Flight Mass Spectrometry" Anal. Chem (2002) 74:6191-6199.

Wang, Z. et al., "Investigation of Spectral Reproducibility in Direct Analysis of Bacteria Proteins by Matrix-assisted Laser Desorption/Ionization Time-of-flight Mass Spectrometry" Rapid Comm. Mass Spec. (1998) 12:456-464.

Welham, K.J. et al., "The Characterization of Micro-organisms by Matirx assisted Laser Desoprtion/Ionization Time-of-flight Mass Spectrometry" Rapid Comm. Mass Spec. (1998) 12:176-180.

Wolters, D.S., M.P. Washburn, and J.R. Yates, III, "An Automated Multidimensional Protein Identification Technology for Shotgun Preteomics" Anal. Chem. (2001) 73:5683-5690.

Yao, Z.-P., P.A. Demirev, and C. Fenselau, "Mass Spectrometry-Based Proteolytic Mapping for Rapid Virus Identification" Anal. Chem. (2002) 74:2529-2534.

Yates, III, J.R. et al., "Peptide Mass Maps: A Highly Informative Approach to Protein Identification" Analytical Biochem (1993) 214:397-408.

Yost, R.A. and C.G. Enke, "Selected Ion Fragmentation with a Tandem Quadrupole Mass Spectrometer" J. Am. Chem. Soc. (1978) 100:2274-2275.

Zamdborg, L. et al., "ProSight PTM 2.0: improved protein identification and characterization for top down mass spectrometry" Nuc. Acids Res. (2007) Web Issue 35:W701-W706.

Zenobi, R. and R. Knochenmuss, "Ion Formation in Maldi Mass Spectrometry" Mass Spec. Rev. (1998) 17:337-366.

* cited by examiner

Putative uncharacterized protein yahO of *E. coli* O157:H7 strain EDL-933
MKIISKMLVGALAFAVTNVYA|AELMTKAEFEKVESQYE
KIGDISTSNEMSTADAKEDLIKKADEKGADVLVLTSGQT
DNKIHGTA|D|IYKKK
MW = 9930.41 Da
Mature protein MW = 7707.62 Da UPF0379 protein yahO of *E. coli* strain K-12
MKIISKMLVGALALAVTNVYA|AELMTKAEFEKVESQYE
KIGDISTSNEMSTADAKEDLIKKADEKGADVLVLTSGQT
DNKIHGTA|N|IYKKK
MW = 9895.41 Da
Mature protein MW = 7706.64 Da

FIG. 13

SEQUENCE LISTING

<160> NUMBER OF SEQ ID NOS: 2

<210> SEQ ID NO 1
<211> LENGTH: 91
<212> TYPE: PRT
<213> ORGANISM: Escherichia coli

```
<400> SEQUENCE: 1

Met Lys Ile Ile Ser Lys Met Leu Val Gly Ala Leu Ala Phe Ala Val
1               5                   10                  15

Thr Asn Val Tyr Ala Ala Glu Leu Met Thr Lys Ala Glu Phe Glu Lys
            20                  25                  30

Val Glu Ser Gln Tyr Glu Lys Ile Gly Asp Ile Ser Thr Ser Asn Glu
        35                  40                  45

Met Ser Thr Ala Asp Ala Lys Glu Asp Leu Ile Lys Lys Ala Asp Glu
    50                  55                  60

Lys Gly Ala Asp Val Leu Val Leu Thr Ser Gly Gln Thr Asp Asn Lys
65                  70                  75                  80

Ile His Gly Thr Ala Asp Ile Tyr Lys Lys Lys
                85                  90

<210> SEQ ID NO 2
<211> LENGTH: 91
<212> TYPE: PRT
<213> ORGANISM: Escherichia coli

<400> SEQUENCE: 2

Met Lys Ile Ile Ser Lys Met Leu Val Gly Ala Leu Ala Leu Ala Val
1               5                   10                  15

Thr Asn Val Tyr Ala Ala Glu Leu Met Thr Lys Ala Glu Phe Glu Lys
            20                  25                  30

Val Glu Ser Gln Tyr Glu Lys Ile Gly Asp Ile Ser Thr Ser Asn Glu
        35                  40                  45

Met Ser Thr Ala Asp Ala Lys Glu Asp Leu Ile Lys Lys Ala Asp Glu
    50                  55                  60

Lys Gly Ala Asp Val Leu Val Leu Thr Ser Gly Gln Thr Asp Asn Lys
65                  70                  75                  80

Ile His Gly Thr Ala Asn Ile Tyr Lys Lys Lys
                85                  90
```

RAPID IDENTIFICATION OF PROTEINS AND THEIR CORRESPONDING SOURCE ORGANISMS BY GAS PHASE FRAGMENTATION AND IDENTIFICATION OF PROTEIN BIOMARKERS

CROSS REFERENCE TO RELATED APPLICATIONS

This application claims priority to U.S. Provisional Patent Application Ser. No. 61/091,039, filed Aug. 22, 2008, and to U.S. Provisional Patent Application Ser. No. 61/191,609 filed Sep. 9, 2008, each of which is incorporated herein by reference in their entirety.

FIELD OF THE INVENTION

The invention relates to the use of laser desorption/ionization mass spectrometry techniques for protein identification, and the detection, identification, and taxonomic classification of the corresponding source organisms from which the proteins are derived.

REFERENCE TO A COMPUTER PROGRAM LISTING APPENDIX

This application includes a computer program listing appendix. The computer program listing appendix is submitted herewith in accordance with 37 C.F.R. 1.96(c), and the material comprising the computer program listing appendix is incorporated herein by reference in its entirety.

BACKGROUND OF THE INVENTION

Rapid, accurate identification of microorganisms is an increasingly important area of research. Indeed, safeguarding of the environment, public health, food production and safety, transportation and national defense all depend on the ability to rapidly and accurately identify pathogens, microbial and otherwise.

For example, foodborne illness is a serious and continuing problem that causes great suffering, death and otherwise exacts enormous societal costs e.g. losses in worker productivity due to illness, recall of food products determined (or suspected) to be contaminated, etc. An estimated 76 million cases of foodborne illness occur each year in the US alone (see e.g., Mead, P. S. et al. (1999) Emerging Infectious Diseases 5(5): 607-625) Frighteningly, foodborne disease caused by bacterial microorganisms is likely to increase with the rise in global temperatures.

Thus, there is a critical need for methods that sensitively detect and rapidly and accurately identify foodborne pathogens before, during and after an outbreak of foodborne illness.

A number of techniques have been developed for detection and identification of microorganisms and other disease agents (e.g., viruses, e.g., Avian influenza virus; protein toxins, prions etc). Pre-eminent among these techniques is mass spectrometry. Mass spectrometry is the science of "weighing" atoms and molecules. Because of its high sensitivity and specificity, mass spectrometry has become a popular technique for detection and taxonomic classification of microorganisms (see e.g., Fenselau C., and Demirev P. A. *Mass Spectrom. Rev.* 2001; 20: 157; Lay Jr. J O. *Mass Spectrom. Rev.* 2001; 20: 172).

As is well known in the art, the use of mass spectrometry (MS) in the analysis of microorganisms is a relatively recent application that was facilitated by the development of two ionization techniques in the late 1980s and early 1990s: electrospray ionization (ESI) (see e.g., Fenn, J. B., et al. (1989). *Science,* 246, 64-71) and matrix-assisted laser desorption/ionization (MALDI) (see e.g., Tanaka, K., et al. (1987) *Second Japan-China Joint Symposium on Mass Spectrometry* (abstract), Osaka, Japan and Karas, M., et al. (1987) *International Journal of Mass Spectrometry and Ion Processes.,* 78, 53-68). MALDI, coupled with time-of-flight (TOF) mass spectrometry, is a powerful tool in "fingerprinting" microorganisms using either cell extracts or lysis of intact cells (see e.g., Cain, T. C., et al. (1994) *Rapid Commun. Mass Spectrom.* 8: 1026; Krishnamurthy, T., et al. (1996) *Rapid Commun. Mass Spectrom.* 10: 883; Krishnamurthy, T., and Ross P L. *Rapid Commun. Mass Spectrom.* 1996; 10:1992; Holland, R. D., et al. (1996) *Rapid Commun. Mass Spectrom.* 10: 1227; Arnold, R., and Reilly, J. (1998) *Rapid Commun. Mass Spectrom.* 12: 630; Welham, K., et al. (1998) *Rapid Commun. Mass Spectrom.* 12: 176; Haag, A., et al. (1998) *J. Mass Spectrom.* 33: 750; Wang Z, et al. (1998) *Rapid Commun. Mass Spectrom.* 1998; 12: 456; Dai Y, et al. *Rapid Commun. Mass Spectrom.* 1999; 13: 73; Ramirez, J., and Fenselau C. (2001) *J. Mass Spectrom.* 36: 929; Mandrell, R. E., et al. (2005) *Applied Environ. Microbio.* 71: 6292; Fagerquist, C. K., et al. (2005) *Anal. Chem.* 77: 4897; and Fagerquist, C. K., et al. (2006) *J. Proteome Research.* 5: 2527). As is known in the art, MALDI-TOF-MS fingerprinting of microorganisms, viruses, proteins and peptides is typically achieved using either pattern recognition or bioinformatic algorithms.

A pattern recognition approach to data analysis typically involves comparison of a MALDI-TOF-MS spectrum from an unknown sample to MALDI-TOF-MS spectra from known, identified entities and searches for similarities in prominent peaks (see e.g., Jarmon, K. H., et al. (2000) *Anal. Chem.* 72: 1217; and Wahl, K. L., et al. (2002) *Anal. Chem.* 2002; 74: 6191). A high similarity between an unknown MS spectrum and a known MS spectrum suggests the identity of the unknown. Unfortunately however, this pattern recognition approach is limited by the fact that it does not rely on actual identification of the peaks in an MS spectrum, but rather on the spectral pattern. Thus, because a particular mass-to-charge ratio (m/z) could be associated with any of a number of biomolecules generated by the microorganism: proteins, nucleic acids, lipids, etc, accuracy of identification using the pattern recognition approach is best achieved with purified molecules.

In addition to the pattern recognition approach, microorganisms may be identified using a bioinformatic approach. The bioinformatic approach to identification of microorganisms by MALDI-TOF-MS, typically involves the use of protein molecular weight (MW) information contained in genomic databases to tentatively assign peaks in a spectrum to specific proteins (see e.g., Demirev, P. A., et al. (1999) *Anal. Chem.* 71: 2732; Peneda, F. J., et al. (2000) *Anal. Chem.* 72: 3739; Demirev, P. A., et al. (2001) *Anal. Chem.* 73: 4566; Yao Z-P, et al. (2002) *Anal. Chem.;* 74: 2529; and Peneda, F. J., et al. (2003) *Anal. Chem.* 75: 3817). As is known in the art, a protein, and by implication the microorganism, are identified when a significant number of peaks in a MS spectrum correspond to the protein MWs derived from the open reading frames (ORFs) of a particular microorganism genome.

The bioinformatic approach may account for simple post-translational modifications, e.g. N-terminal methionine cleavage (see e.g., Demirev et al. (2001) supra), but many proteins of interest have extensive post translational modifications. Thus, since protein biomarker identification relies solely on protein MW, identification of any individual biomarker may only at best, be considered as a tentative assignment.

Pattern recognition and bioinformatic MALDI-TOF-MS analysis work well for the identification of pure strains. Unfortunately however, data analysis using either of these methods is complicated when multiple bacterial microorganisms are present in a sample. Indeed, MALDI-TOF-MS analysis of bacterial mixtures typically results in the detection of protein biomarkers from multiple bacteria, thus making the pattern of m/z peaks presented in an MS spectrum difficult to interpret. Similarly, the bioinformatic approach may tentatively assign spectral peaks as being proteins on the basis of predicted protein MWs from the ORFs found in multiple bacterial genomes. Furthermore, the presence (and/or relative abundance) of proteins from multiple microorganisms affects on protein ionization efficiency resulting in changes in the proteins ionized and detected. Thus, analysis of samples containing multiple bacterial (or other microorganisms) presents increased challenges for MALDI-TOF-MS.

To overcome the increased challenges for MALDI-TOF-MS when multiple organisms are present, protein biomarkers are either enzymatically digested and the resulting tryptic peptides are analyzed by MS or by MS/MS ("bottom-up proteomics). Alternatively, the intact protein is fragmented in the gas phase to obtain sequence-specific information from fragment ions ("top-down" proteomics).

Until recently, gas phase fragmentation was only accomplished using very expensive mass spectrometric instrumentation and/or complicated gas phase ion dissociation techniques. However, the development of MALDI tandem mass spectrometry (MALDI-TOF-TOF) instruments has made gas phase fragmentation less cumbersome to undertake (see e.g., Medzihradszky K F, et al. *Anal. Chem.* 2000:72:552). MALDI-TOF-TOF instruments may be used to fragment small and modest-sized intact proteins (>5 kDa) (see e.g., Lin M, et al. *Rapid Comm. Mass Spectrom.* 2003; 17: 1809). Thus, a MALDI-TOF-TOF instrument may provide a "fingerprint" of a bacterial microorganism in MS mode, and also sequence-specific information of protein biomarkers by MS/MS (see e.g., Demirev, P. A., et al. (2005) *Anal. Chem.* 2005; 77: 7455).

Because the amino acid sequence of a protein is often unique to a microbial strain, identification of a single protein biomarker is often sufficient for identification of the microorganism. In addition, whereas multiple microorganisms may complicate MALDI-TOF-MS analysis, MS/MS of specific protein biomarkers allows identification of unique protein biomarkers that are specific to a particular microorganism and thus facilitates thr identification of a microorganism in a mixed sample.

The potential of tandem mass spectrometry techniques such as e.g., MALDI-TOF-TOF, for the rapid and accurate identification of proteins and their source organisms is only beginning to be realized. Indeed, given the proliferation of biological threats from diseases, pests, and bioterrorism, the increasing numbers of proteomes in public databases, (which continues to grow at an exponential rate) and the potential forensic applications (see e.g., Goldsmith, J. (1990) *A crime lab for animals—National Fish and Wildlife Forensics Laboratory, Ashaland, Oreg.—Special Issue: Environmental Restoration* Whole Earth Review, Spring, 1990) one can rest assured that the value and importance of tandem mass spectrometry techniques for the identification of proteins will continue to grow.

Thus, what is needed in the art, are better matching algorithms and improved scoring schemes which facilitate ease of use and which will improve the accuracy, and rapidity of tandem mass spectrometry techniques thereby facilitating their utility.

Fortunately, as will be clear from the following disclosure, the present invention provides for these and other needs.

SUMMARY OF THE INVENTION

One embodiment of the present invention provides a method for identification of an unknown protein comprising: (i) comparing mass-to-charge (m/z) fragment ion peaks from an mass spectrum of the unknown protein to that of m/z fragment ion peaks from mass spectra of known protein sequences; and (ii) matching the m/z fragment ion peaks from the mass spectrum of the unknown protein to the m/z fragment ion peaks from the mass spectra of known protein sequences to provide mass spectrometry peak matches; (iii) scoring the mass spectrometry peak matches using a USDA peak matching algorithm thereby providing a USDA peak matching score; and (iv) ranking the USDA peak matching score from highest to lowest; wherein the highest USDA peak matching score constitutes an identification of the unknown protein.

In one exemplary embodiment the USDA peak matching algorithm is USDA peak matching algorithm α, which has the formula:

$$\text{USDA}\alpha \text{ Score} = 100 \times \frac{2 \times (\text{Number of peak matches})}{(\text{Number of peaks in the mass spectrum of the unknown protein} + \text{Number of peaks in the mass spectrum of known protein sequences})}.$$

In another exemplary embodiment the USDA peak matching algorithm is USDA peak matching algorithm β, which has the formula:

$$\text{USDA}\beta \text{ Score} = 100 \times \frac{\text{Number of peak matches}}{(\text{Number of } MS/MS \text{ fragment ion peaks})}.$$

In one exemplary embodiment, the difference between the highest USDA peak matching score and the second highest USDA peak matching score is equal to or greater than 2.

In another exemplary embodiment, the mass spectra are members selected from the group consisting of MS spectra and MS/MS spectra.

In one exemplary embodiment, the mass spectrum of the unknown protein is an MS spectrum and the mass spectra of known protein sequences are MS spectra of known proteins.

In another exemplary embodiment, the mass spectrum of the unknown protein is an MS/MS spectrum and the mass spectra of known protein sequences are members of the group consisting of in silico MS/MS spectra generated from a genomically-derived database of protein sequences and MS/MS spectra of known proteins.

In one exemplary embodiment, the mass spectra of known protein sequences are in silico MS/MS spectra generated from a genomically-derived database of protein sequences.

In one exemplary embodiment, the method further comprises: (v) confirming that the highest USDA peak matching score constitutes an identification of the unknown protein. The confirming comprises: plotting the difference in m/z (Δm/z) between an MS/MS fragment ion of the unknown protein and its matched fragment ion from the in silico MS/MS spectra generated from a genomically-derived database of protein sequences as a function of MS/MS fragment ion m/z, thereby providing a plot of Δm/z vs MS/MS fragment ion m/z, wherein a correct protein identification is indicated when the plot of Δm/z vs MS/MS fragment ion m/z reveals a characteristic systematic error related to the inherent calibration error of the mass analyzer, and wherein an incorrect protein identification is indicated when the plot of Δm/z vs MS/MS fragment ion m/z reveals statistically random error.

In another exemplary embodiment, the method further comprises: (v) confirming that the highest USDA peak matching score constitutes an identification of the unknown protein. In one exemplary embodiment, the confirming comprises: performing steps (i)-(iv), wherein the in silico MS/MS spectra generated from a genomically-derived database of protein sequences are limited to spectra generated by displaying only fragment ions generated by fragmentation at an aspartate (D) residue, glutamate (E) residue or proline (P) residue, and (vi) observing that the difference between the highest USDA peak matching score and the second highest USDA peak matching score is equal to or greater than the difference between the highest USDA peak matching score and the second highest USDA peak matching score obtained when steps (i)-(iv) are performed using in silico MS/MS spectra generated from a genomically-derived database of protein sequences that are not limited spectra generated by displaying only fragment ions generated by fragmentation at an aspartate (D) residue, glutamate (E) residue or proline (P) residue, thereby confirming that the highest USDA peak matching score constitutes an identification of the unknown protein.

In another exemplary embodiment, the confirming comprises: performing steps (i)-(iv), wherein the in silico MS/MS spectra generated from a genomically-derived database of protein sequences are limited to spectra generated by displaying only fragment ions generated by fragmentation at an aspartate (D) residue, and (vi) observing that the difference between the highest USDA peak matching score and the second highest USDA peak matching score is equal to or greater than the difference between the highest USDA peak matching score and the second highest USDA peak matching score obtained when steps (i)-(iv) are performed using in silico MS/MS spectra generated from a genomically-derived database of protein sequences that are not limited spectra generated by displaying only fragment ions generated by fragmentation at an aspartate (D) residue, thereby confirming that the highest USDA peak matching score constitutes an identification of the unknown protein.

In one exemplary embodiment, the unknown protein is a protein toxin.

In another exemplary embodiment, identification of the unknown protein is used to identify the source organism from which the unknown protein derived. In one exemplary embodiment, the source organism is a member selected from the group consisting of: viruses, microorganisms, insects, plants, and animals. In another exemplary embodiment, the source organism is a microorganism selected from the group consisting of: bacteria and fungi. In another exemplary embodiment, the source organism is a bacterium that is a member selected from the group consisting of *Campylobacter, Escherichia coli, Listeria* and *Salmonella*.

Another embodiment of the invention provides a computer readable storage medium storing instructions that, when executed by a computer, causes the computer to perform a method for identification of an unknown protein comprising: (i) comparing mass-to-charge (m/z) fragment ion peaks from an mass spectrum of the unknown protein to that of m/z fragment ion peaks from mass spectra of known protein sequences; and (ii) matching the m/z fragment ion peaks from the mass spectrum of the unknown protein to the m/z fragment ion peaks from the mass spectra of known protein sequences to provide mass spectrometry peak matches; (iii) scoring the mass spectrometry peak matches using a USDA peak matching algorithm thereby providing a USDA peak matching score; and (iv) ranking the USDA peak matching score from highest to lowest; wherein the highest USDA peak matching score constitutes an identification of the unknown protein.

In one exemplary embodiment the USDA peak matching algorithm is USDA peak matching algorithm α, which has the formula:

$$\text{USDA}\alpha \text{ Score} = 100 \times \frac{2 \times (\text{Number of peak matches})}{(\text{Number of peaks in the mass spectrum of the unknown protein} + \text{Number of peaks in the mass spectrum of known protein sequences})}.$$

In another exemplary embodiment the USDA peak matching algorithm is USDA peak matching algorithm β, which has the formula:

$$\text{USDA}\beta \text{ Score} = 100 \times \frac{\text{Number of peak matches}}{(\text{Number of } MS/MS \text{ fragment ion peaks})}.$$

In one exemplary embodiment, the difference between the highest USDA peak matching score and the second highest USDA peak matching score is equal to or greater than 2.

In another exemplary embodiment, the mass spectra are members selected from the group consisting of MS spectra and MS/MS spectra.

In one exemplary embodiment, the mass spectrum of the unknown protein is an MS spectrum and wherein the mass spectra of known protein sequences are MS spectra of known proteins.

In one exemplary embodiment, the mass spectrum of the unknown protein is an MS/MS spectrum and the mass spectra of known protein sequences are members of the group consisting of in silico MS/MS spectra generated from a genomically-derived database of protein sequences and MS/MS spectra of known proteins. In another exemplary embodiment, the mass spectra of known protein sequences are in silico MS/MS spectra generated from a genomically-derived database of protein sequences.

In another exemplary embodiment, the method further comprises: (v) confirming that the highest USDA peak matching score constitutes an identification of the unknown protein, wherein the confirming comprises: plotting the difference in m/z (Δm/z) between an MS/MS fragment ion of the unknown protein and its matched fragment ion from the in silico MS/MS spectra generated from a genomically-derived database of protein sequences as a function of MS/MS fragment ion m/z, thereby providing a plot of Δm/z vs MS/MS fragment ion m/z, wherein a correct protein identification is indicated when the plot of Δm/z vs MS/MS fragment ion m/z reveals a characteristic systematic error related to the inherent calibration error of the mass analyzer, and wherein an incorrect protein identification is indicated when the plot of Δm/z vs MS/MS fragment ion m/z reveals statistically random error.

In another exemplary embodiment, the method further comprises: (v) confirming that the highest USDA peak matching score constitutes an identification of the unknown protein, wherein the confirming comprises: performing steps (i)-(iv), wherein the in silico MS/MS spectra generated from a genomically-derived database of protein sequences are limited to spectra generated by displaying only fragment ions generated by fragmentation at an aspartate (D) residue, glutamate (E) residue or proline (P) residue, and (vi) observing that the difference between the highest USDA peak matching score and the second highest USDA peak matching score is equal to or greater than the difference between the highest USDA peak matching score and the second highest USDA peak matching score obtained when steps (i)-(iv) are performed using in silico MS/MS spectra generated from a genomically-derived database of protein sequences that are not limited spectra generated by displaying only fragment ions generated by fragmentation at an aspartate (D) residue, glutamate (E) residue or proline (P) residue, thereby that the highest USDA peak matching score constitutes an identification of the unknown protein.

In another exemplary embodiment, the confirming comprises: performing steps (i)-(iv), wherein the in silico MS/MS spectra generated from a genomically-derived database of protein sequences are limited to spectra generated by displaying only fragment ions generated by fragmentation at an aspartate (D) residue, and (vi) observing that the difference between the highest USDA peak matching score and the second highest USDA peak matching score is equal to or greater than the difference between the highest USDA peak matching score and the second highest USDA peak matching score obtained when steps (i)-(iv) are performed using in silico MS/MS spectra generated from a genomically-derived database of protein sequences that are not limited spectra generated by displaying only fragment ions generated by fragmentation at an aspartate (D) residue, thereby confirming that the highest USDA peak matching score constitutes an identification of the unknown protein.

In one exemplary embodiment, the unknown protein is a protein toxin.

In another exemplary embodiment, identification of the unknown protein is used to identify the source organism from which the unknown protein derived. In another exemplary embodiment, source organism is a member selected from the group consisting of: viruses, microorganisms, insects, plants, and animals. In another exemplary embodiment, the source organism is a microorganism selected from the group consisting of: bacteria and fungi. In another exemplary embodiment, the source organism is a bacterium that is a member selected from the group consisting of *Campylobacter, Escherichia coli, Listeria* and *Salmonella*.

Other features, objects and advantages of the invention will be apparent from the detailed description which follows.

BRIEF DESCRIPTION OF THE DRAWINGS

FIG. 13 Primary amino acid sequence of the putative uncharacterized protein yahO of the pathogenic *E. coli* O157: H7 (EDL-933 strain) MKIISKMLVGALAFAVTNVYA-AELMTKAEFEKVESQYEKIGDISTSNEMSTADAKED-LIKKADEKGADVLVLTSGQTDNKIHGTADIYKKK (SEQ ID NO:1) and the UPF0379 protein yahO of the non-pathogenic *E. coli* (K-12 strain) MKIISKMLVGALALAVT-NVYAAELMTKAEFEKVESQYEKIGDISTSNEMSTAD-AKEDLIKKADEKGADVLVLTSGQTDNKIHGTANIYK-KK (SEQ ID NO:2). Both proteins are post-translationally modified with a 21 residue signal peptide (boxed). Differences in amino acids between the two proteins are highlighted in bold. The D↔N amino acid substitution results in a protein MW difference of 1 Da in the mature protein. Such slight differences in protein biomarker MW are nearly impossible to detect by MALDI-TOF-MS, however sequence-specific fragmentation by MS/MS allows these two proteins (and their source microorganisms) to be differentiated.

DETAILED DESCRIPTION OF THE INVENTION

Definitions

Figure 1:
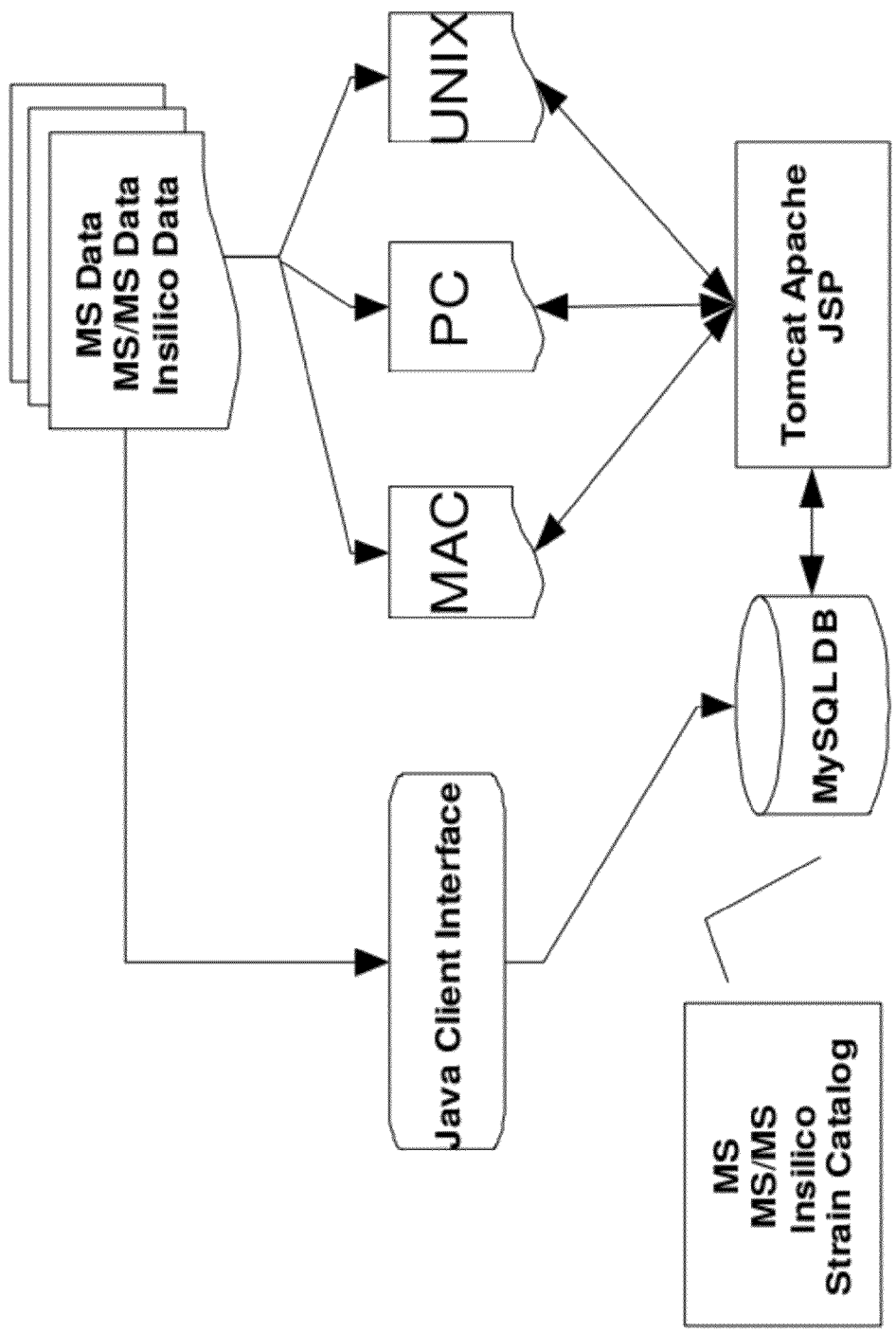
FIG. 1 provides a general overview of the framework for the USDA mass spectrometry comparison software.

The expression "mass spectrum" as used herein, refers in general, to an intensity vs. m/z (mass-to-charge ratio) plot that represents the result of a chemical analysis. Hence, the mass spectrum of a sample is a pattern representing the distribution of charged molecules by mass-to-charge ratio in a sample. Thus, an "MS spectrum" as used herein, refers to a mass spectrum produced by mass spectrometer having a single mass analyser and single detector. In contrast, an "MS/MS spectrum" as used herein, refers to a mass spectrum produced by a tandem mass spectrometer.

The expression "matching the m/z fragment ion peaks from a mass spectrum of the unknown protein to the m/z fragment ion peaks from the mass spectra of known protein sequences" as used herein refers to a procedural step used by a person having ordinary skill in the art to make an identification of an unknown protein. Typically, "matching the m/z fragment ion peaks from a mass spectrum of the unknown protein to the m/z fragment ion peaks from the mass spectra of known protein sequences" refers to comparing the m/z of fragment ions that result from ionization and fragmentation of an intact unknown protein to the theoretical/calculated m/z of in silico generated fragment ions of known protein sequences. The theoretical/calculated in silico molecular masses are based on the known atomic masses of the atoms which make up the known amino acid sequence, and as such, the calculated masses are considered to be "exact". The measured m/z of fragment ions from the ionized and fragmented unknown protein is not "exact" but, rather, is subject to the mass accuracy of a given mass analyzer. The mass accuracy of the mass analyzer may be determined and used to compare measured m/z values to those calculated "exact" masses. If the measured m/z value is within the analyzer's known uncertainty (mass accuracy and precision), then the comparison is considered to be a match (i.e. a "peak match"). If the measured m/z value differs from the calculated in silico m/z value by more than the instruments precision, then the comparison results in no match being found.

Thus, "identification of an unknown protein" occurs when the m/z fragment ion peaks from a mass spectrum of the unknown protein "match" the m/z fragment ion peaks from the mass spectra of a known protein sequence.

The expression "USDA peak matching score" as used herein, refers to the number of measured m/z values which match calculated "exact" m/z values (within the instrument's measurement precision). In an exemplary embodiment, a "USDA peak matching score" is obtained by applying a "USDA peak matching algorithm". In an exemplary embodiment "USDA peak matching algorithm" is the "USDA peak matching algorithm alpha ($\alpha$)", which has the following formula:

$$\text{USDA}\alpha \text{ Score} = 100 \times \frac{2 \times (\text{Number of peak matches})}{\begin{array}{c}(\text{Number of peaks in the mass spectrum of}\\ \text{the unknown protein} +\\ \text{Number of peaks in the mass spectrum of}\\ \text{known protein sequences})\end{array}}$$

In another exemplary embodiment, the "USDA peak matching algorithm" is the "USDA peak matching algorithm beta ($\beta$)" which has the following formula:

$$\text{USDA}\beta \text{ Score} = 100 \times \frac{\text{Number of peak matches}}{(\text{Number of } MS/MS \text{ fragment ion peaks})}$$

Thus, unless specifically referred to otherwise, the expression "USDA peak matching score" refers inclusively to USDA peak matching scores obtained using the "USDA peak matching algorithm alpha ($\alpha$)" and/or the "USDA peak matching algorithm beta ($\beta$)".

The expression "ranking the USDA peak matching score from highest to lowest" as used herein, refers to ordering of scores from highest to lowest where the highest reflects the greatest number of matches between measured m/z values and calculated masses from a known sequence.

The expression "difference between highest USDA peak matching score and second highest USDA peak matching score" as used herein, refers to the result obtained by subtracting the second highest USDA peak matching score from the highest USDA peak matching score.

The term "in silico" as used herein refers generally, to processes taking place via computer calculations. In recent years, the DNA sequences of hundreds of organisms have been decoded and stored in databases. Indeed, the amount of information stored in "in silico databases" continues to grow exponentially as more genomes are sequenced and more proteomes are characterized. Thus, a large body of "in silico" genomic information has been obtained and stored and the amount continues to grow. The information stored in an "in silico database" may be analyzed to determine inter alia genes that encode polypeptides and/or the sequence of the polypeptides encoded by the genes. Such protein sequences are referred to herein as "genomically-derived". Thus, in an exemplary embodiment, "in silico" protein sequences comprise a "genomically-derived" protein sequence deduced by computer calculations based on a known DNA sequence. Alternatively, an "in silico" protein sequence may comprise the actual protein sequence as determined by a physical protein sequencing method e.g., Edman degradation, de novo sequencing by mass spectrometry, etc.

The expression "in silico MS/MS spectrum" as used herein refers to a theoretical or hypothetical tandem mass spectrum generated by a computer based on known protein sequences.

The term "in silico" fragment ion as used herein, takes on the meaning as typically used in the art and thus, refers to theoretical protein fragments generated by fragmentation performed in silico on known protein sequences. In some exemplary embodiments an in silico MS/MS spectrum shows theoretical fragment ions generated at every residue. In other exemplary embodiments, an in silico MS/MS spectrum shows theoretical fragment ions generated at selected residues.

The expression "mass spectra of known protein sequences" as used herein, refers to theoretical mass spectra generated in silico by calculated fragmentation of genomically-derived protein sequences and/or to mass spectra that are physically generated from known proteins.

The expression "mass spectrum of an unknown protein" as used herein, refers to the experimentally obtained mass spectrum of a protein whose identity has not been determined with certainty. Typically, an experimentally acquired mass spectrum of a protein rarely shows fragment ions at every residue because the fragmentation efficiency at every residue is not the same.

The expression "source organism" as used herein, refers to an organism that has provided or that is used to provide a sample and hence proteins for analysis by laser desorption ionization mass spectrometry (e.g., Matrix-Assisted Laser Desorption/Ionization MALDI) as disclosed herein. In an exemplary embodiment a source organism is a microorganism. In another exemplary embodiment a source organism is a bacterium. In still other exemplary embodiments a source organism is a plant, an animal, an insect, a virus or a human.

The expression "providing a plot of $\Delta$m/z vs fragment ion m/z" as used herein, refers to plotting of the difference between the measured m/z and the calculated exact m/z of an analyte (e.g., a protein) as a function of analyte ion m/z. Instrument calibration involves comparing the observed masses of a mixture of known standards (e.g., protein standards) to their calculated exact masses. Any discrepancy between a standard's measured m/z and its known m/z is considered error. The m/z error ($\Delta$m/z, i.e. the difference between the measured m/z and the actual m/z) is plotted as a function of analyte ion m/z.

The expression "characteristic systematic error related to the inherent calibration of the instrument" as used herein, refers to systematic error as revealed by a linear regression analysis fit of the relevant data (e.g., $\Delta$m/z vs fragment ion m/z). Similarly, the expression "statistically random error" as used herein, refers to statistically random error as defined by a linear regression analysis fit of data. Regression analysis is well known in the art (see e.g., Draper, N. R. and Smith, H. *Applied Regression Analysis*, Wiley Series in Probability and Statistics (1998); Richard A. Berk, Regression Analysis: A Constructive Critique, Sage Publications (2004); David A. Freedman, Statistical Models: Theory and Practice, Cambridge University Press (2005))

The terms "polypeptide," and "protein" are used interchangeably herein to refer to a functional polymer of amino acid residues. Typically a functional protein folds cooperatively and comprises multiple secondary structural elements e.g., $\alpha$-helices or $\beta$-pleated sheets, that interact in the final structure. The smallest known protein is TRP-Cage, a functional protein of only 20 amino acids (see e.g., Jonathan W. Neidigh et al. (2002) *Nature Structural Biology* 9:425-430). However, as used herein, the term "protein" typically refers to a polymer of amino acid residues that is above about 5 kDa molecular weight. A polymer of amino acid residues that is below about 5 kDa molecular weight is typically referred to as a "peptide". Thus, as used herein, a "peptide" is not a "protein", and a "peptide" is not a "polypeptide".

The term "amino acid" as used herein, refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, $\gamma$-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids are referred to herein by either their commonly known three letter symbols or by the one-letter symbols recommended by the IUPAC-IUB Biochemical Nomenclature Commission.

The term "microorganism" is used herein, refers to is an organism that is microscopic. In its broadest sense the term "microorganism" refers to a diverse array of organisms including, but not limited to bacteria, fungi, archaea, and protists, as well as some microscopic plants and animals e.g., plankton.

The term "virus" as used herein, refers to sub-microscopic infectious agents that are typically unable to grow or reproduce outside a host cell. Typically a viral particle, or virion, comprises genetic material e.g., DNA or RNA, within a protective protein coat called a capsid. Viruses infect all cellular life forms and are grouped into animal, plant and bacterial types, according to the type of host infected.

The term "protein toxin" as used herein, refers to refers to any polypeptide that is deleterious to humans or other mammals when it is injected, ingested, inhaled or when contacted with the skin.

I. Introduction:

Rapid, accurate identification of proteins and the source organisms from which they are derived is increasingly valuable as threats to biosecurity of the environment, public health, food production and safety, transportation and national defense all continue to increase. Rapid, accurate identification of proteins also facilitates the work of forensic scientists concerned with the protection of endangered species and/or with solving of personal crime.

Since the identity of proteins connects directly to the genetic identity of the source organism (e.g., a pathogenic organism; protein toxin e.g., prion; blood sample; etc). Identification of a protein may be used to successfully identify the source organism (e.g., a bacterium, an endangered species, etc) from which it is derived. Fortunately, variations in protein biomarker amino acid composition due to non-synonymous mutations of the biomarker gene result in variations in protein molecular weight (MW) across genus, species and strains. The ability to tap into this information on a precise level is thus invaluable for the accurate identification of source organisms.

Improvements in the science of protein identification are always needed and welcome. Thus, an exemplary embodiment of the invention provides a method for rapid and accurate identification of proteins using laser desorption ionization mass spectrometry methods e.g., MALDI. In one exemplary embodiment, identification of the protein permits identification of the source organism from which the identified protein is derived. In another exemplary embodiment, the method comprises a peak-matching/scoring mathematical algorithm (the USDA peak matching algorithm) for comparison of MS/MS spectra of protein biomarkers and in silico MS/MS spectra of protein sequences contained in a database.

In one exemplary embodiment, a USDA peak matching algorithm is the USDA α peak matching algorithm and has the formula:

$$\text{USDA}\alpha \text{ Score} = 100 \times \frac{2 \times (\text{Number of peak matches})}{(\text{Number of peaks in the mass spectrum of the unknown protein} + \text{Number of peaks in the mass spectrum of known protein sequences})}$$

In another exemplary embodiment, a USDA peak matching algorithm is the USDA β peak matching algorithm and has the formula:

$$\text{USDA}\beta \text{ Score} = 100 \times \frac{\text{Number of peak matches}}{(\text{Number of } MS/MS \text{ fragment ion peaks})}$$

In one exemplary embodiment, the USDA peak matching algorithm (either or α or β) is incorporated into a computer software program such that a MS/MS spectrum can be compared to thousands of in silico MS/MS spectra in seconds thereby allowing rapid identification of a protein and its source organism.

In another exemplary embodiment, the method further comprises steps for confirming the correctness of the protein identification, thereby ensuring accuracy. In one exemplary embodiment, confirming the correctness of the protein identification is achieved through error analysis. In this embodiment, the error analysis comprises analyzing the difference in mass-to-charge (m/z) between the MS/MS fragment ions and their putative in silico fragment ion "matches". Correct identifications are characterized in that the error is typically limited to systematic error caused by the inherent calibration error of the mass analyzer. In contrast, incorrect identifications are characterized by random error caused by false "matches".

In another exemplary embodiment, confirming the correctness of the protein identification is achieved by performing an identification of an unknown protein by comparing the MS/MS spectrum of the unknown protein to a full array of MS/MS in silico spectra of protein sequences contained in a database, and then performing the identification by comparing the MS/MS spectrum of the unknown protein to a set of MS/MS in silico spectra of protein sequences contained in the same database which are limited to those spectra which arise when the fragmentation occurs only at aspartic acid (D) glutamic acid (E) and proline (P) residues; and observing that the difference between the highest and the second highest USDA peak matching scores is the same or greater than the difference between the highest and the second highest USDA peak matching scores obtained in the identification using the full array of MS/MS in silico spectra of protein sequences contained in the database.

In still another exemplary embodiment, confirming the correctness of the protein identification is achieved by performing an identification of an unknown protein by comparing the MS/MS spectrum of the unknown protein to a full array of MS/MS in silico spectra of protein sequences contained in a database, and then performing the identification by comparing the MS/MS spectrum of the unknown protein to a set of MS/MS in silico spectra of protein sequences contained in the same database which are limited to those spectra which arise when the fragmentation occurs only at aspartic acid (D) residues; and observing that the difference between the highest and the second highest USDA peak matching scores is the same or greater than the difference between the highest and the second highest USDA peak matching scores obtained in the identification using the full array of MS/MS in silico spectra of protein sequences contained in the database.

Enzymatic digestion of a protein is not required for analysis and identification of proteins using the disclosed methods. Thus, in one exemplary embodiment, proteins are analyzed without prior enzymatic digestion. However, in another exemplary embodiment, proteins are analyzed following enzymatic digestion.

In one embodiment of the invention, the methods and algorithms disclosed herein are contained in a computer readable storage medium thereby providing instructions that when executed by a computer, causes the computer to perform a method for identification of an unknown protein.

II. Identification of Proteins Using Laser Desorption Ionization Mass Spectrometry.

A. General Laser Desorption Ionization Mass Spectrometry Methods

Mass spectrometry is a sensitive and specific analytical technique that is increasingly being developed for detection, identification and characterization of proteins. Thus, mass spectrometry is also becoming a powerful tool for the identification of pathogenic bacterial microorganisms, viruses, and protein toxins and also finds use in proteomics and forensic science.

The methods disclosed herein utilize routine techniques in the field of mass spectrometry. Basic texts disclosing general mass spectrometry methods include e.g., *Mass Spectrometry: A Textbook*, by Jürgen H. Gross, (2002, 2004, 2006) Springer, and *Mass Spectrometry: Principles and Applications* by Edmond de Hoffmann, and Vincent Stroobant, (2002) John Wiley and Sons Ltd, (each of which is incorporated herein by reference). Laser Desorption/Ionization is disclosed e.g., in *Laser Desorption Ionization Mass Spectrometry of Bioorganic Molecules* by: Michael Karas, and Ute Bahr (1993) *Methods in Molecular Biology* Vol. 17 pages 215-228 Springer.

Laser desorption/ionization mass spectrometry methods which produce singly, or occasionally doubly charge ions are suitable for use in the protein identification methods disclosed herein. In addition to MALDI, any method that is capable of mass isolating and fragmenting singly charged protein ions in the gas phase is suitable for use in the protein identification methods disclosed herein.

Laser desorption/ionization methods known in the art which have the ability to produce singly charged and sometimes doubly charged ions include, but are not limited to SELDI (see e.g. Surface-enhanced laser desorption/ionization (SELDI), Ning Tang, et al. (2004) Mass Spectrometry Reviews, 23:34-44); Infrared laser desorption/ionization on silicon (see e.g., Bhattacharya S H et al. (2002) Anal Chem. May 1; 74(9):2228-31); Laser desorption/ionization mass spectrometry on porous silicon (see e.g., Seetharaman Vaidyanathan, et al. (2007) Rapid Communications in Mass Spectrometry 21(13): 2157-2166); MALDI (see e.g., Tanaka, K., et al. (1987) supra and Karas, M., et al. (1987) supra) etc.

The methods disclosed herein for identification of an unknown protein are not suitable for use with ionization methods that produce multiply charged ions. Such methods include, but are not limited to e.g., electrospray ionization (ESI) (see e.g., Fenn, J. B., et al. (1989) *Science,* 246, 64-71).
B. Matrix-Assisted Laser Desorption/Ionization (MALDI)

In an exemplary embodiment, the laser desorption/ionization mass spectrometry method is matrix-assisted laser desorption/ionization (MALDI). MALDI is a soft ionization technique, that is useful for, inter alia the analysis of biomolecules (see e.g., Cain, T. C., et al. (1994) supra; Krishnamurthy, T., et al. (1996) supra; Krishnamurthy, T., and Ross P L. (1996) 10:1992 supra; Karas, M. & Hillenkamp, F. (1988) *Analytical Chemistry,* 60, 2299-2301; Karas, M, et al. (1987). *Int. J. Mass Spectrom. Ion Proc.* 78:53-68; Lancaster, K. S., et al. (2006) *Anal Chem.,* 78, 4990-4997) and large organic molecules generally (see e.g., Karas, M.; Bahr, U. (1990). "Laser Desorption Ionization Mass Spectrometry of Large Biomolecules". *Trends Anal. Chem.* 9: 321-5).

MALDI involves embedding analyte molecules in a matrix of a weak organic acid that are solids at room temperature (e.g. α-cyano-4-hydroxycinnamic acid). MALDI matrices typically absorb strongly in the ultraviolet electromagnetic spectrum (e.g. 337 nm or 355 nm, etc.). Typically, a pulsed nitrogen (at 337 nm) or pulsed solid state YAG laser (at 355 nm) is used to irradiate a dried spot of organic acid matrix that is embedded with analyte. These lasers have repetition rates from 2-100 Hz with a pulse width of 10 nanoseconds. The strong absorption of the matrix at the laser wavelength results in an explosive desorption from the target plate of matrix and analyte molecules into the gas phase.

In a process that is still not well understood, analyte molecules are protonated (or deprotonated). The MALDI ionization process typically results in singly charged protonated analytes (in positive ion mode). Higher charge states are possible but these typically have less signal intensity. In the case of peptides and proteins, protonation typically occurs at the side-chains of basic residues (e.g., arginine, lysine, histidine).

Because relatively low charge states are produced by MALDI the mass-to-charge (m/z) ratio of proteins is typically beyond the mass range of most mass analyzers. Thus, the type of a mass spectrometer most widely used with MALDI is the TOF (time-of-flight mass spectrometer) since this mass analyzer has a theoretically unlimited mass range.

MALDI has been used for the identification of proteins isolated through gel electrophoresis or other purification methods (see e.g., Demirev, P. A., et al. *Anal. Chem.* 1999; 71: 2732; Peneda, F. J., et al. *Anal. Chem.* 2000; 72: 3739; Demirev, P. A., et al. *Anal. Chem.* 2001; 73: 4566; Yao Z-P, et al. *Anal. Chem.* 2002; 74: 2529; Peneda, F. J., et al. *Anal. Chem.* 2003; 75: 3817). MALDI is also used for peptide mass fingerprinting by methods known in the art (see e.g., Pappin D J, et al. (1993). *Curr. Biol.* 3 (6): 327-32; Henzel W J, et al. (1993). *Proc. Natl. Acad. Sci. U.S.A.* 90 (11): 5011-5; Mann M, et al. (1993). *Biol. Mass Spectrom.* 22 (6): 338-45; James P, et al. (1993). *Biochem. Biophys. Res. Commun.* 195 (1): 58-64; Yates J R, et al. (1993) *Anal. Biochem.* 214 (2): 397-408).

Tandem MALDI e.g., MALDI-TOF-TOF instruments have been used to fragment small to medium-sized proteins (see e.g., Lin M, et al. (2003) supra). MALDI has also been used for identification of *Bacillus* spores by fragmenting their protein biomarkers using a tandem MALDI mass spectrometer and analyzing the sequence-specific fragment ions generated by comparison to in silico fragment ions derived from protein amino acid sequences from open reading frames of genomic databases (see e.g., Demerev et al. (2005) *Anal Chem* 77:7455). Identifications were tested for significance by a p-value calculation, which provides a probability that an identification occurred randomly (see e.g., Demerev et al. (2005) supra).

At one time, mass spectrometry was only practiced by relatively small number of highly trained specialists. However, a revolution in mass spectrometry was triggered by the development of two ionization techniques developed in the late 1980s and early 1990s: matrix-assisted laser desorption/ionization or MALDI (Tanaka, Ido, Akita, Yoshida & Yoshida, 1987), (Karas, Bachmann, Bahr & Hillenkamp, 1987), (Karas & Hillenkamp, 1988), and electrospray ionization or ESI (Fenn, Mann, Meng, Wong, & Whitehouse, 1989). The impact that these two inventions dramatically extended the development of mass spectrometry and its application to the analysis of large biomolecules including peptides, proteins, nucleic acids and complex carbohydrates.

With the rapid development of genomic sequencing (i.e. "next-generation"), the speed of genomic sequencing, and the ability to acquire longer DNA sequence "reads", will allow almost any strain of microorganism to be completely sequenced in a relatively short period of time. This capability means that the number of strains of a genus, species, subspecies, sub-type of microorganism that will be genomically sequenced will increase significantly beyond what is currently possible. With this ever increasing amount of genomic data being made available in public and private databases, the number of unique protein amino acid sequences (open reading frames or ORFs of genomic data) is expected to increase together with the genomic sequencing efforts. In consequence, it is critical that, as the volume of genomic and proteomic data increases, the mathematical algorithms used to analyze and exploit such data be as computationally efficient as possible.

Fortunately, the USDA peak matching algorithms disclosed herein are demonstrably faster in computation speed than other method currently used in the art e.g., p-value calculation (see e.g., Demirev et al. (2005) *Anal. Chem.* 77:7455). Fortunately, in using the faster USDA peak matching algorithms, accuracy is not sacrificed for speed. Indeed, the USDA peak matching algorithms are faster and give comparable results in scoring/ranking of protein/organism identifications as that obtained by other methods more complicated scoring algorithms known in the art e.g., p-value calculation (see e.g., Tables 1A, 2A, 3A).

The difference in algorithm computation speeds is further enhanced (in favor of the USDA peak matching algorithms) when only residue-specific in silico fragment ions (e.g. D,E, P-specific fragment ions) are used for comparison to MS/MS fragment ions (see e.g., Tables 1B, 2B, 3B). Under these circumstances, the USDA algorithm computation speed is cut by at least about half whereas the p-value computation speed is reduced by only about ~20% at best. The increased speed and accuracy of protein identification provided by residue-specific analysis has not heretofore been appreciated by others (see e.g., Demirev et al. (2005) *Anal. Chem.* 77:7455). Indeed, in the past it has typically been assumed, that fragment ions could be generated, theoretically, at every residue of a protein.

In some exemplary embodiments, the USDA mass spectrometry comparison software uses plots and "fits" fragment ion m/z error as a function of fragment ion m/z to confirm the correctness of the USDA peak matching algorithm identification. Such a confirmatory analysis has heretofore not been utilized or demonstrated. Thus, the methods disclosed herein are simpler, faster, more accurate and more complete than other currently available methods.

1. Sample Preparation for MALDI

Samples may be prepared for MALDI ionization by any method known in the art (see e.g., Onnerfjord, P., Ekström, S., Bergquist, J., Nilsson, J., Laurell, T., Marko-Varga, G. (1999) *Rapid Commun Mass Spectrom.*, 13, 315-322).

Typically, a purified sample of the analyte compound (e.g. peptide, protein, small molecule) is dissolved in an aqueous solution at a concentration of picomole ($10^{-12}$ mole) per μL ($10^{-6}$ L) or lower.

The MALDI matrix of choice (see below) is dissolved in a separate aqueous solution (e.g. 2:1 water/acetonitrile) to make a saturated (or sub-saturated) solution of matrix. Typically, this solution is acidified with an acid such as e.g., 0.1% of trifluoroacetic acid (TFA) however, any suitable acidifier can be used in an effective concentration. As is known in the art, acidification facilitates protonation of analyte molecules during the desorption/ionization process.

In one exemplary embodiment, roughly equal aliquots of matrix solution and analyte solution are mixed together and then spotted onto a stainless steel MALDI target. The spot is allowed to dry and the target is inserted into the ionization source of the mass spectrometer.

In another exemplary embodiment, a one μL aliquot of the matrix is spotted onto the stainless steel MALDI target and allowed to dry before a one μL aliquot of the sample is overlayed on top of the spot of dried matrix. The re-dissolved spot is allowed to dry before inserting the target into the mass spectrometer.

In still another exemplary embodiment, the sample is spotted the on the stainless steel target, and allowed to dry and then spotting the matrix on top of the dried spot of sample (see e.g., Onnerfjord, Ekström, Bergquist, Nilsson, Laurell, Marko-Varga, 1999).

MALDI works best when contaminants (e.g. salts, small molecules, etc.) are removed from the sample before MALDI preparation. Salts, in particular, interfere with ionization by MALDI. Sample clean-up using high performance liquid chromatography (HPLC) or dialysis helps to reduce salts and small molecule contaminants that may interfere with MALDI ionization of the analyte of interest.

2. Protein Extraction

Protein extraction may be accomplished using any suitable technique known in the art. Typically the technique chosen depends on the nature of the protein one wishes to extract. The skilled artisan will appreciate those factors that influence extraction of their protein of interest and will choose their extraction techniques accordingly. For example, proteins may be hydrophilic or hydrophobic or have regions that display both properties. Cytosolic proteins (because they reside in the aqueous cytosol of the cell) are often the easiest proteins to extract because they are hydrophilic and thus dissolve easily in aqueous solutions. Cytosolic proteins are also often high copy proteins so their relative abundance in the cellular proteome is high. In consequence, protein biomarkers of bacterial cells are often high copy cytosolic proteins. Extraction of cytosolic proteins typically involves nothing more difficult than rupturing the cellular membrane (or cell wall) to release the cytosolic proteins into the surrounding protein extraction medium (e.g. water/acetonitrile).

Cell membrane or cell wall disruption is accomplished by any technique known in the art, e.g. bead-beating (see e.g., Mandrell, R. E., Harden, L. A., Bates, A., Miller, W. G., Haddon, W. F., & Fagerquist, C. K. (2005). *Appl Environ Microbiol.*, 71, 6292-6307; high pressure disruption (see e.g., Smejkal, G. B., Robinson, M. H., Lawrence, N. P., Tao, F., Saravis, C. A., Schumacher, R. T. (2006) *J. Biomol. Tech.*, 17, 173-175; or sonication (see e.g., Balasundaram, B., Pandit, A. B. (2001) *Biotechnol Bioeng.*; 75, 607-614).

3. MALDI Matrices

In general, the identity of suitable matrix compounds is determined to some extent by trial and error. However, some considerations are helpful in guiding the skilled practitioner (see e.g., K. Strupat, et al. (1991) International Journal of Mass Spectrometry and Ion Processes Vol. 111, 1991, Pages 89-102; Beavis R C, and Chait B T (1989). *Rapid Commun. Mass Spectrom.* 3 (12): 432-5; Karas, M. et al. (1987). *Int J Mass Spectrom Ion Proc* 78: 53-68.).

In general, exemplary MALDI matrices are low molecular weight (e.g., 100-200 Da) weak organic acids which are solid at room temperature but absorb strongly at ultraviolet light at wavelengths, e.g. 337 nm (nitrogen laser) or 355 nm (3rd-harmonic of a solid state YAG laser).

Exemplary MALDI matrices are also typically are functionalized with polar groups, allowing their use in aqueous solutions. The most popular MALDI matrices for ionizing peptides and proteins are α-cyano-4-hydroxycinnamic acid (abbreviated CHCA or CCA), 2,5-dihydroxybenzoic acid (abbreviated DHB), trans-4-hydroxy-3-methoxy-cinnamic acid (common name: ferulic acid) and 3,5 dimethoxy-4-hydroxy-cinnamic acid (common name: sinapinic acid). CHCA is considered a "hot" matrix because during laser vaporization/desorption this matrix appears deposit significant amounts of energy into the peptide or protein which can result in dissociation of the peptide or protein ion after it exits the ionization chamber. CHCA also generates doubly and triply protonated (charged) analytes in addition to singly protonated (charged) analytes, thus, it should be used with care in order to be suitable for use with the method disclosed herein for identification of an unknown protein. At the other end of the MALDI matrix spectrum is sinapinic acid which is considered to be a "cold" matrix. Use of sinapinic acid as a MALDI matrix tends to generate only singly protonated ions as well as high molecular weight proteins. In consequence, sinapinic acid is particularly suited to ionization of higher molecular weight proteins, e.g., above about 10 kDa.

C. Mass Spectrometry

Mass spectrometry is the science of "weighing" (or measuring the mass) of atoms and molecules. As is known in the art, the applications of mass spectrometry are numerous, ranging from measuring very precisely the abundances of atomic isotopes of elements found in the periodic table, to measuring with high resolution and mass accuracy the mass of large biomolecules, e.g. proteins (see e.g., Grayson, M. A. (2002) *Measuring Mass*, Chemical Heritage Foundation).

1. Tandem Mass Spectrometry

In an exemplary embodiment, the methods disclosed herein utilize tandem MALDI mass spectrometry. As is well known in the art, tandem mass spectrometry (or MS/MS) involves coupling two (or more) mass analyzers in tandem in order to selectively interrogate individual analyte ions observed in MS analysis.

A popular tandem mass spectrometer is the triple quadrupole (see e.g., Yost, R. A., Enke, C. G. (1978) *J. Amer. Chem. Soc.*, 100:2274-2275). When used in MS/MS mode, the first quadrupole of a triple quadrupole instrument is operated so as to allow only ions of a particular m/z to transit into the second quadrupole mass analyzer. This is called mass isolation or mass selection. The mass-selected ions are fragmented in a second quadrupole typically by collision-activated dissociation (CAD). The fragment ions generated are then analyzed and detected by the third quadrupole mass analyzer. Because of mass-selection/isolation, the fragment ions generated in the second quadrupole are linked to the analyte precursor ions selected by the first quadrupole.

The principles of MS/MS have been extended to a number of instrument platforms e.g., time of flight (TOF). TOF/TOF mass spectrometry is known in the art (see e.g., U.S. Pat. No. 6,300,627).

In an exemplary embodiment, a method of identifying an unknown protein employs MALDI TOF/TOF mass spectrometry. Briefly, MS/MS using a MALDI-TOF-TOF instruments involves using the first TOF mass analyzer to separate ions in space and time. Because ions are separated on TOF instruments on the basis of their relative velocities and this is related to an ion's m/z, a timed ion "gate" is used to mass-select/isolate ions of a specific m/z. Only ions of a specific m/z (with a specific velocity and thus arrival time at the "gate") are allowed to pass from the first TOF mass analyzer to a collision cell. All other ions arriving either "too early" or "too late" are deflected from entering the collision cell. Thus, mass-selection/isolation is attained.

The mass selected/isolated ions are dissociated in the collision cell by high energy collision-activated dissociation (CAD) or by post-source dissociation (PSD) or by laser-induced dissociation (LID). On TOF-TOF instruments, collision energies of 1-2 keV are possible. PSD involves the dissociation of ions as a result of the energy deposited into the analyte ion at the ionization source. After precursor ion fragmentation, fragment ions are analyzed by the second TOF mass analyzer (see e.g., Medzihradszky, K. F., et al. (2000). *Anal. Chem.*, 72, 552-558).

a. Error Analysis

In an exemplary embodiment, the method comprises confirming that the highest USDA peak matching score constitutes an identification of the unknown protein. In this embodiment the correctness of the identification is confirmed by plotting the difference in m/z (Δm/z) between an MS/MS fragment ion of the unknown protein and its matched fragment ion from the in silico MS/MS spectra generated from a genomically-derived database of protein sequences as a function of MS/MS fragment ion m/z. The resulting plot of Δm/z vs MS/MS fragment ion m/z is subjected to a linear regression analysis fit of the data. Linear regression analysis is known in the art (see e.g., Skoog, D. A. & West, D. M. (1986). *Analytical Chemistry*, 4th edition.)

Briefly, linear regression analysis is the process by which a "best" fit straight line is fitted to data plotted in two dimensions (e.g. x-dimension and y-dimension). In an exemplary embodiment, such an analysis is used in creating a calibration curve for a mass spectrometer. The simplest linear regression is the method of least squares. The method of least squares is a regression analysis that minimizes the square of the vertical displacement (residuals) of the data points from the line that is being fitted to the data. This process generates the "best" fit of the line to the data points (Skoog & West, 1986, supra).

A correct protein identification is indicated when the plot of Δm/z vs MS/MS fragment ion m/z reveals a characteristic systematic error related to the inherent calibration error of the mass analyzer.

An incorrect protein identification is indicated when the plot of Δm/z vs MS/MS fragment ion m/z reveals statistically random error.

In an exemplary embodiment, prior to running a sample, the mass spectrometer is tuned to maximize sensitivity, resolution and mass accuracy. Typically, this involves either manually or automatically adjusting the instrument's ion optics using a known standard. This process ensures that the ionization source, mass analyzer and detector are all functioning properly. As part of this process, the mass analyzer is also calibrated.

Calibrating the mass analyzer ensures that mass measurement is within the operating specifications of the instrument. As the skilled artisan will appreciate, instrument calibration in MS mode involves comparing the observed masses of a mixture of known standards to their actual masses. Any discrepancy between a standard's measured m/z and its known m/z is considered error. The m/z error or Δm/z (i.e. difference between the measured m/z and the actual m/z) is plotted as a function of analyte ion m/z. A linear regression analysis (e.g., higher order curve fitting) is used to generate a calibration curve that is then applied to the mass assignment of any subsequent data collected to correct for inaccuracies in the mass analyzer's performance.

As the skilled artisan also appreciates, it is not unusual, even after calibration, for a mass analyzer to experience "drift", i.e. the instrument calibration is no longer correcting for a mass analyzer's slight inaccuracies in mass measurement. In an exemplary embodiment, mass analyzer "drift" is due to changes in the temperature of the room in which the instrument is housed, however other causes could be in play. TOF, TOF-TOF and hybrid quadrupole-TOF or ion trap-TOF instruments, are particularly susceptible to calibration "drift" due to changes in room temperature. In consequence, the instrument may require re-calibration daily (or more often) if there is a significant change in room temperature.

In an exemplary embodiment, the "drift" in calibration of TOF-based mass spectrometry instrumentation is exploited with respect to peptide and protein identification that involves comparison of an MS/MS spectrum to in silico MS/MS spectra.

It has been shown that a tryptic peptide (with a known amino acid sequence) analyzed using a hybrid quadrupole-TOF mass spectrometer in MS/MS mode generates an MS/MS spectrum that, when "matched" to its correctly identified in silico MS/MS peptide spectrum, results in a linear correlation (using linear regression analysis) between the fragment ion m/z error as a function of fragment ion m/z, and that this linear correlation was not observed when the MS/MS spectrum was "matched" to an incorrect in silico MS/MS peptide spectrum.

However, since it was concluded experimentally that the "drift" in the instrument calibration of the TOF mass analyzer of the quadrupole-TOF instrument was caused by changes in the temperature of the instrumentation room (see e.g., Taylor, J. A. & Johnson, R. S (2001) *Analytical Chemistry*, 73, 2594-2604), this linear correlation for the correct in silico peptide identification was simply incorporated into de novo peptide sequencing software (as an internal standard, i.e. trypsin autolysis peptides) to correct for the calibration "drift" of the TOF mass analyzer on the quadrupole-TOF instrument due to room temperature changes.

Thus, although a linear "fit" of the fragment ion m/z error has been used to correct for calibration error of a TOF mass analyzer, it has not been appreciated before the instant disclosure that a linear "fit" of the fragment ion m/z error could be used to "identify" or "confirm the identity" of a protein and/or peptide sequence to that of an in silico sequence in a database.

Thus an exemplary embodiment of the invention provides a comparison of fragment ions generated from MS/MS of mature, intact proteins from cell lysates analyzed using a tandem TOF instrument to in silico fragment ions from protein amino acid sequence in a database. The difference in m/z between the MS/MS fragment ions and their putative in silico fragment ion "matches" are plotted as a function of the MS/MS fragment ion m/z. A linear or least-squares fit of such data is used to confirm the correctness of the USDA peak matching algorithm identification. In an exemplary embodiment, a correct identification displays evidence of a linear correlation between m/z error vs. fragment ion m/z whereas an incorrect identification will display poor correlation (i.e. random error) between m/z error vs. fragment ion m/z.

b. Residue Specific Analysis

In an exemplary embodiment, the method comprises confirming that the highest USDA peak matching score constitutes an identification of the unknown protein. In this embodiment the correctness of the identification is confirmed by performing the method while limiting the in silico MS/MS spectra generated from a genomically-derived database of protein sequences to spectra generated by displaying only fragment ions generated by fragmentation at an aspartate (D) residue, glutamate (E) residue, or proline (P) residue. If the difference between the highest USDA peak matching score and the second highest USDA peak matching score is equal to or greater than the difference between the highest USDA peak matching score and the second highest USDA peak matching score obtained when the method is performed without the limitation to D, E, and/or P residues this confirms the identification of the unknown protein.

As discussed more extensively below, in an exemplary embodiment, the method for identifying an unknown protein is contained within computer readable storage medium storing instructions that, when executed by a computer, causes the computer to perform a method for identification of an unknown protein.

In one exemplary embodiment, the software allows an "MS/MS to In Silico Comparison" to compare MS/MS fragment ions to all possible in silico MS/MS fragment ions or to only residue-specific in silico MS/MS fragment ions.

In another exemplary embodiment, the software allows an "MS/MS to In Silico Comparison" to compare MS/MS fragment ions to a subset of all possible in silico MS/MS comprising certain selected residue-specific in silico MS/MS fragment ions. In one exemplary embodiment, the comparison is executed by the software that compares the subset of in silico MS/MS residue-specific in silico MS/MS fragment ions comprising D,E,P-specific in silico MS/MS fragment ions to the MS/MS fragment ions. In another exemplary embodiment, the comparison is executed by the software that compares the subset of in silico MS/MS residue-specific in silico MS/MS fragment ions comprising D-specific in silico MS/MS fragment ions to the MS/MS fragment ions.

Although it has been shown experimentally that singly protonated proteins are more likely to fragment at the polypeptide backbone at sites that are adjacent to an aspartic acid (D), glutamic acid (E) or proline (P) (see e.g., Lin, M., et al. (2003) *Rapid Commun. Mass Spectrom.* 17:1809-1814.), until the discovery by the present inventors, it was not heretofore appreciated that this experimental observation could be exploited into a method or software algorithm to specifically identify a protein (and its source organism) on the basis of a comparison of MS/MS fragment ions to residue-specific in silico MS/MS fragment ions.

Incorporating residue specific analysis into the methods for identifying an unknown protein, as disclosed herein, significantly increases the ability to correctly and accurately identify an unknown protein as reflected in a USDA peak matching score (i.e., USDAα Score and/or USDAβ Score). Indeed, the absolute value of the USDA peak matching score is increased as well as the relative value of the highest USDA peak matching score relative to the second highest USDA peak matching score(s) and the USDA peak matching scores of other incorrect identifications.

Without being bound by theory, it is believed that the reason for this increase is that, if it is known experimentally that a particular protein (or proteins) will preferentially fragment at particular sites along the polypeptide backbone due to specific residues adjacent to such cleavage sites, then the software can be directed to include only those residue-specific in silico MS/MS fragment ions for comparison to the experimentally measured MS/MS fragment ions, i.e. they are fewer in silico MS/MS fragment ions that are involved in the comparison to MS/MS fragment ions, thus increasing the numerical value of the "USDA Score". Such selectivity not only increases the identification score of the correct identification, but also reduces the computation time of the analysis because fewer in silico MS/MS fragment ions are being compared.

D. Databases

1. In Silico Databases

Constructing an In Silico MS/MS Database

In an exemplary embodiment, an in silico MS/MS database is constructed to retrieve the amino acid sequences of all bacterial proteins having a protein molecular weight the same as the protein biomarker molecular weight within a specified mass tolerance (e.g. 10,000±5 Da). Bacterial protein amino acid sequences can be downloaded from public web-based database servers (e.g. ExPASY proteomics server, available through Swiss Institute of Bioinformatics). In an exemplary embodiment, the TagIdent software tool at the Expasy website allows the retrieval of proteins on the basis of taxonomic identification of the source organism as well as protein pI, protein molecular weight and any sequence tag information (e.g., a short sequence of adjacent amino acid residues in the protein) if it available. TagIdent searches the public databases of UniProtKB/Swiss-Prot and/or UniProtKB/TrEMBL for all proteins which correspond to the specified search parameters.

In an exemplary embodiment, all of the proteins that fit the specified search criteria are compiled into a single large FASTA file. This multi-protein sequence FASTA file is then imported into a mass spectrometry-based proteomics software (e.g. the a commercially available GPMAW, ©Lighthouse Data). Mass spectrometry-based proteomics software e.g., GPMAW, converts each protein amino acid sequence contained in the FASTA file into a series of in silico MS/MS fragment ions. The fragment ions are identified by their m/z, ion type/number (e.g. $b_{52}$, $y_{44}$, $a_{27}$, $y_{32}$-17, $b_{92}$-18, etc.) and the two amino acid residues immediately adjacent to the polypeptide cleavage site that generated the fragment ion.

Each protein sequence (and its associated in silico MS/MS fragment ion information) is exported by the mass spectrometry-based proteomics software e.g., GPMAW, software as a separate datafile. Thus, a single multi-protein sequence FASTA file containing 700 protein sequences will result in 700 in silico MS/MS datafiles when processed by GPMAW. These in silico MS/MS datafiles are then imported into the in silico MS/MS database of the USDA mass spectrometry comparison software using Java client ("InSilicoUploadjar", i.e. a binary file [jar file] that is interpreted by the Java Runtime Environment or JRE) which was created to import/upload automatically multiple in silico MS/MS data files to the MySQL database of the USDA mass spectrometry comparison software. This software program is operated independently of the Tomcat Apache (TA)/Java Server Pages (JSP) of the USDA mass spectrometry comparison software. Once the in silico files are imported into the In silico MS/MS Database of the USDA mass spectrometry comparison software, the data can be displayed or compared against MS/MS acquired experimentally.

Figure 8:
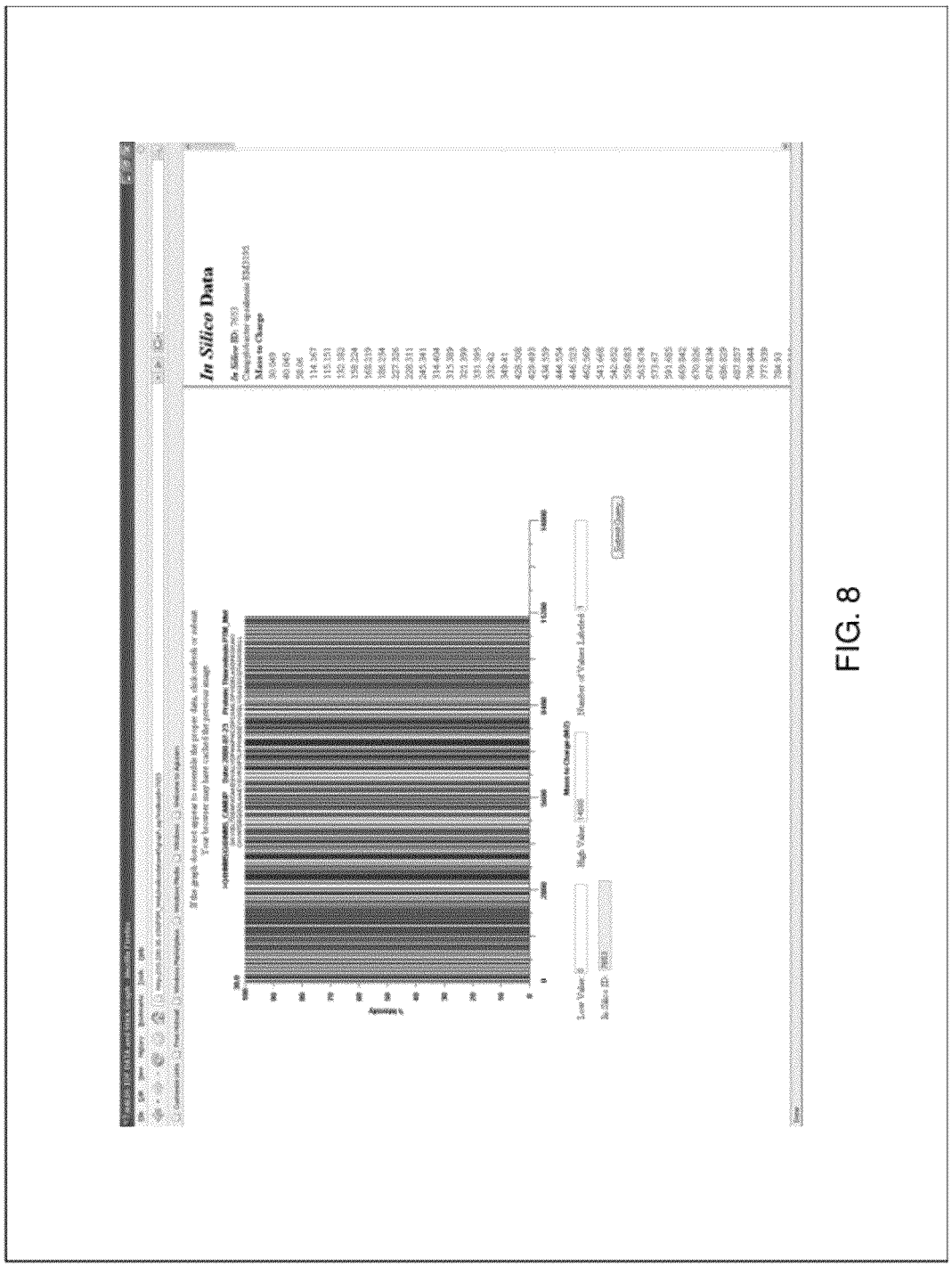
FIG. 8 shows the in silico MS/MS spectrum (as displayed in the USDA software window) of the protein thioredoxin of *Campylobacter upsaliensis* (strain RM3195).

Display of an in silico MS/MS spectrum looks very much like a "barcode" because each in silico MS/MS fragment ion has a 100% relative intensity as shown in FIG. 8. In contrast, an experimentally acquired MS/MS spectrum will have fragment ions whose intensity can vary from 0 to 100% as that shown in FIG. 6.

2. Mass Spectra of Known Proteins

In an exemplary embodiment, the amino acid sequence of a protein is determined by genetic or genomic sequencing of the gene whose product is protein. In another exemplary embodiment, the genomically-derived amino acid sequence of protein is determined and/or confirmed by proteomic techniques such as Edman sequencing or "bottom-up" or "top-down" mass spectrometry-based proteomic techniques.

An MS and/or MS/MS spectrum of a protein whose identity was previously determined based on genomic sequencing of the protein's gene or Edman sequencing of the protein's N-terminal sequence, is an exemplary mass spectrum of a known protein.

3. Temporary Databases

A "temporary database" is simply tabulated data that is stored temporarily in random access memory (RAM). Processing such tabulated data when it is stored in RAM is significantly faster than processing the same data when it is stored on a hard drive.

E. Computer Software

1. Overview

In an exemplary embodiment, the invention provides a computer readable storage medium storing instructions that, when executed by a computer, causes the computer to perform a method for identification of an unknown protein. The method for identifying the unknown protein comprises: (i) comparing mass-to-charge (m/z) fragment ion peaks from an mass spectrum of the unknown protein to that of m/z fragment ion peaks from mass spectra of known protein sequences; and (ii) matching the m/z fragment ion peaks from the mass spectrometry spectrum of the unknown protein to the m/z fragment ion peaks from the mass spectrometry spectra of known protein sequences to provide mass spectrometry peak matches; (iii) scoring the mass spectrometry peak matches using the formula:

$$\text{USDA}\alpha \text{ Score} = 100 \times \frac{2 \times (\text{Number of peak matches})}{(\text{Number of peaks in the mass spectrum of the unknown protein} + \text{Number of peaks in the mass spectrum of known protein sequences})}$$

thereby providing a USDAα peak matching score; and (iv) ranking the USDAα peak matching score from highest to lowest; wherein the highest USDAα peak matching score constitutes an identification of the unknown protein.

In another exemplary embodiment, the invention provides a computer readable storage medium storing instructions that, when executed by a computer, causes the computer to perform a method for identification of an unknown protein. The method for identifying the unknown protein comprises: (i) comparing mass-to-charge (m/z) fragment ion peaks from an mass spectrum of the unknown protein to that of m/z fragment ion peaks from mass spectra of known protein sequences; and (ii) matching the m/z fragment ion peaks from the mass spectrometry spectrum of the unknown protein to the m/z fragment ion peaks from the mass spectrometry spectra of known protein sequences to provide mass spectrometry peak matches; (iii) scoring the mass spectrometry peak matches using the formula:

$$\text{USDA}\beta \text{ Score} = 100 \times \frac{\text{Number of peak matches}}{(\text{Number of } MS/MS \text{ fragment ion peaks})}$$

thereby providing a USDAβ peak matching score; and (iv) ranking the USDAβ peak matching score from highest to lowest; wherein the highest USDAβ peak matching score constitutes an identification of the unknown protein.

In one exemplary embodiment, the instructions on the computer readable storage medium comprise a computer software program for the identification of proteins by analysis of fragment ions generated from gas phase fragmentation of singly charged protein ions generated by matrix-assisted laser desorption/ionization (MALDI) and analyzed by tandem time-of-flight (TOF) mass spectrometry (MS/MS). Prior enzymatic digestion of the proteins is not required. The software also provides instructions for performing a pair-wise comparison of an unknown MALDI-TOF-MS spectrum to that of known MALDI-TOF-MS spectra and rank spectra according to spectral similarity thereby enabling a user to identify an unknown spectrum.

In one exemplary embodiment, the USDA mass spectrometry comparison software (which in exemplary embodiments may utilize either the USDAα or the USDAβ peak matching algorithms) is written in JAVA and JSP computer language. However, in other exemplary embodiments the software is written in C, C++, PHP, Assembly or any other web-based software languages known in the art. To ensure that the web based/cross platform component is available a web server based language is utilized e.g., ASP, JSP, PHP, etc.

The code for software embodiments is disclosed herein in the computer program listing appendix. The USDA mass spectrometry comparison software (which in exemplary embodiments may utilize either the USDAα or the USDAβ peak matching algorithms) comprises the following features, functionalities and attributes:

A web browser interface and associated databases that utilize MySQL for database management.

The USDA mass spectrometry comparison software enables efficient entry, deletion, retrieval and searching of organism (e.g., microorganism) isolate information, e.g. in the case of a microorganism taxonomy, origin, source, etc.

The USDA mass spectrometry comparison software enables the entry of ASCII formatted m/z and intensity MS and MS/MS data files to databases for subsequent searching, retrieval or deletion.

The USDA mass spectrometry comparison software enables the entry of single data files (or multiple data files) of ASCII formatted m/z MS/MS in silico data files to a database for subsequent searching, retrieval or deletion.

The USDA peak matching algorithms enable comparison of the mass-to-charge (m/z) of fragment ion peaks from a MS/MS spectrum to the m/z of fragment ions of an in silico MS/MS spectra of proteins. The software compares fragment ions of in silico MS/MS spectra to fragment ions of an MS/MS spectrum of an unknown protein when the mass of the protein falls within a pre-specified mass tolerance (e.g. ±1.0 Th; ±2.0 Th; ±3.0 Th; ±4.0 Th; ±5.0 Th; wherein Th is Thomson the unit of m/z) of the precursor protein ion. When the difference between the m/z of a fragment ion in a MS/MS spectrum of an unknown protein and the m/z of a fragment ion in an in silico MS/MS spectrum fall within the set pre-specified mass tolerance (e.g. ±2.5 Th) it is a "match". The USDAα peak matching algorithm has the formula:

$$\text{USDA}\alpha\ \text{Score} = 100 \times \frac{2 \times (\text{Number of peak matches})}{\begin{array}{c}(\text{Number of peaks in the mass spectrum of}\\ \text{the unknown protein} + \\ \text{Number of peaks in the mass spectrum of}\\ \text{known protein sequences})\end{array}}$$

The USDAβ peak matching algorithm has the formula:

$$\text{USDA}\beta\ \text{Score} = 100 \times \frac{\text{Number of peak matches}}{(\text{Number of } MS/MS \text{ fragment ion peaks})}$$

The highest scoring protein/microorganism identification obtained using either the USDAα or USDAβ peak matching algorithms, that is significantly higher than the second highest scoring protein/microorganism identification constitutes a presumptive correct identification. In an exemplary embodiment, significantly higher is a difference in score between the highest scoring identification and the second highest scoring identification that is equal to or greater than 2. In another exemplary embodiment, significantly higher is a difference in score between the highest scoring identification and the second highest scoring identification that is equal to or greater than 3. In another exemplary embodiment, significantly higher is a difference in score between the highest scoring identification and the second highest scoring identification that is equal to or greater than 4 or more.

For convenience, in an exemplary embodiment, a probability-based significance testing algorithm (e.g., p-value calculation see Demirev et al. (2005) supra) is incorporated into the USDA mass spectrometry comparison software. The USDA peak matching score and the p-value calculation are completely independent. In this embodiment, the results of each calculation are displayed side-by-side in the identification results window. In this embodiment, the USDA mass spectrometry comparison software enables a user to rank the protein/microorganism identifications according to either the USDA peak matching score or the probability-based significance testing algorithm.

Thus, the USDA mass spectrometry comparison software enables a user to enter and retrieve data, and search or delete a database containing ASCII formatted m/z and intensity MALDI-TOF-MS data. In an exemplary embodiment, the USDA mass spectrometry comparison software performs a pair-wise comparison of a MALDI-TOF-MS spectrum from an unknown protein to that of MALDI-TOF-MS spectra from samples of known proteins and to rank the spectra according to spectral similarity thereby providing a taxonomic classification of the unknown protein and hence of the source organism from which the unknown protein is derived. The algorithms used for such a pairwise comparison are disclosed above. In another exemplary embodiment, the USDA mass spectrometry comparison software assigns the identity of m/z peaks in a MALDI-TOF-MS spectrum by comparison to another database of theoretical protein molecular weights derived from genomic data (e.g., open-reading frames or ORFs).

In one exemplary embodiment, for each unknown protein "identification", the USDA mass spectrometry comparison software displays a side-by-side comparison of the measured fragment ion m/z and the m/z of an in silico fragment ions to which it matches. When the identification is correct, a plot of the m/z error (Δm/z), i.e. the difference in m/z between the measured fragment ions and their in silico fragment ion matches, reveals a characteristic systematic error caused by the inherent calibration error of the instrument. Incorrect protein identifications, in contrast, are seen to display only statistically random error caused by false "matches". The confirmation of the correctness of the unknown protein identification by systematic error is independent of the mathematical algorithm used for unknown protein identification.

2. Software/Database Structure and Functionality

FIG. 1 provides a general overview of the framework for the USDA mass spectrometry comparison software. The software stored on a computer readable storage medium provides instructions that when executed by a computer, causes the computer to perform a method for identification of an unknown protein. The instructions comprising the USDA mass spectrometry comparison software utilizing either the USDAα or USDAb peak matching algorithms are provided herein in the computer program listing appendix.

Figure 2:
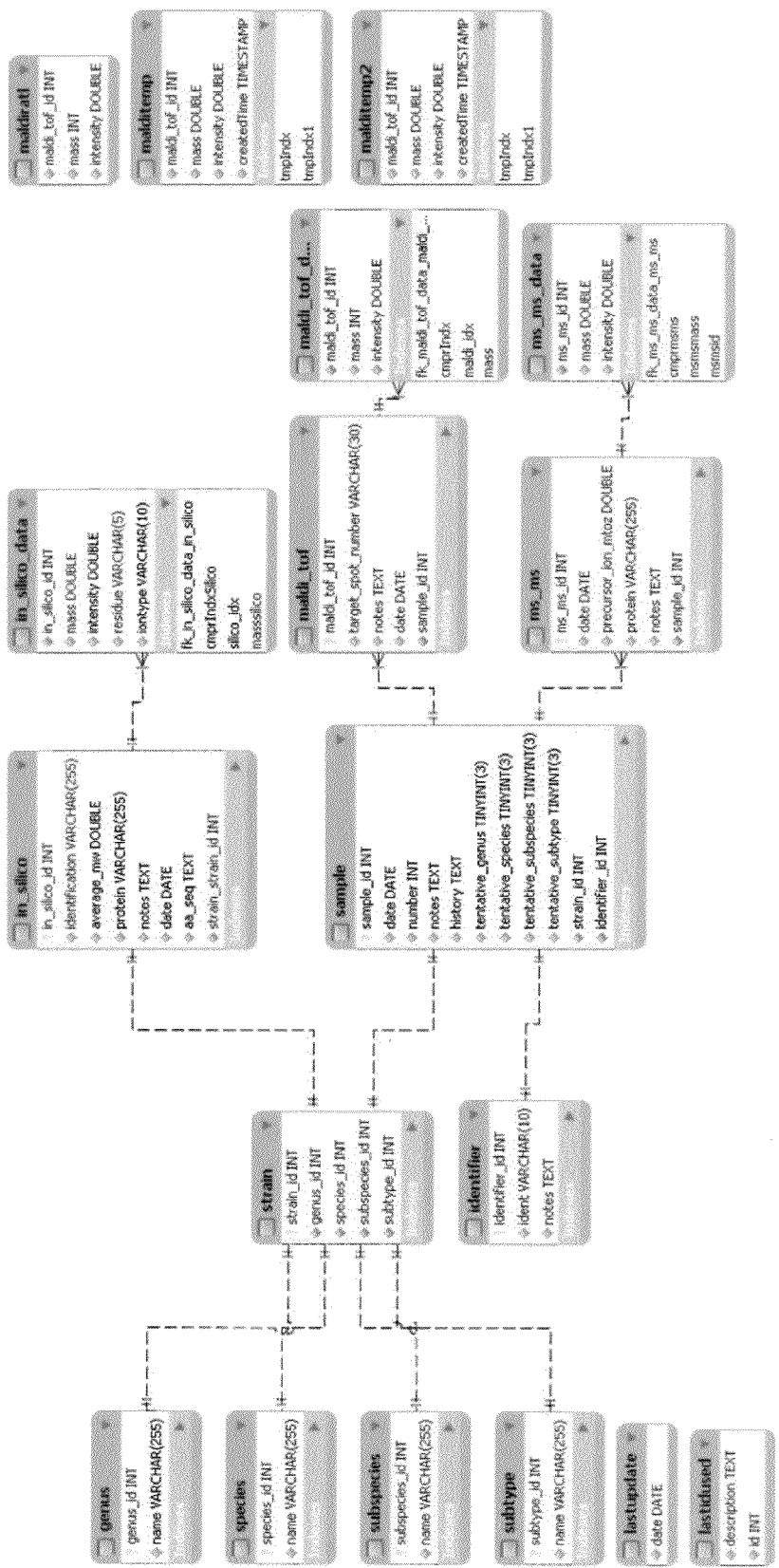
FIG. 2 shows the database model describing how the data is stored.

FIG. 2 shows the database model describing how the data is stored. A MySQL Database Management System (MySQL DBMS) is used as the back-end (i.e. software that indirectly provides support for a client) for the archival/retrieval/analysis software developed for protein/microorganism identification by mass spectrometry (MS) and tandem mass spectrometry (MS/MS). A Tomcat Apache (TA) web server delivers the user/operator interface to any computer platform (e.g. PCs, Macintosh, Unix). The front-end (i.e. the software with which the user/operator interacts) was created using Java Server Pages (JSP). A second front-end is a Java client (i.e. a binary file [jar file] that is interpreted by the Java Runtime Environment or JRE) which was created to upload automatically multiple in silico MS/MS data files to the MySQL DB and is operated independently of the TA/JSP server. The web client allows the user/operator to search, archive, retrieve and edit microorganism strain information as well as perform spectral similarity analysis of MS and MS/MS data of microorganism proteins or toxin proteins, e.g. comparison of $MS_a \leftrightarrow MS_b$ or $MS/MS_a \leftrightarrow MS/MS_b$ or MS/MS↔In Silico MS/MS. The web client also allows a user/operator to display plots of archived MS, MS/MS and in silico MS/MS data. The web client also facilitates visual comparison of putative "matched" data by displaying stacked or mirrored plots of MS↔MS, MS/MS↔MS/MS or MS/MS↔In Silico MS/MS data.

3. Spectral Similarity Analysis

Figure 3:
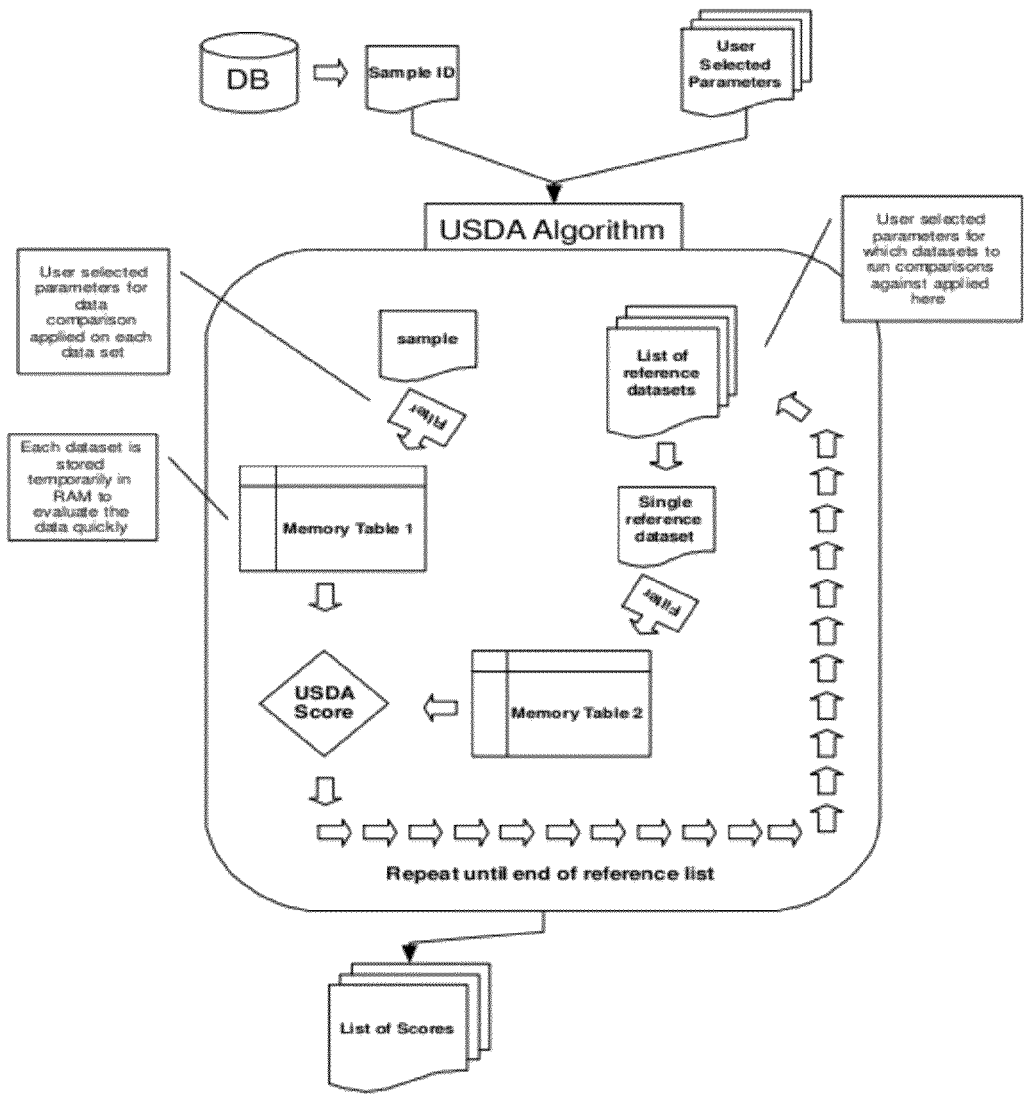
FIG. 3 describes the USDA mass spectrometry comparison software process used to compare each dataset.

FIG. 3 describes the USDA mass spectrometry comparison software process used to compare each dataset. Spectral similarity analysis of MS or MS/MS data involves multiple steps. First, the user/operator selects the parameters under which the data analysis is to be conducted. Exemplary parameters include, but are not limited to: 1. the specific microorganisms MS/MS data as determined by a primary key (i.e. an integer that uniquely identifies a dataset); 2. the mass range to be compared; 3. the minimum relative intensity threshold of MS peaks to be compared; 4. the tolerance of the mass-to-charge (Δm/z) when comparing the m/z of two fragment ion peaks; 5. the scoring algorithm to be used in the analysis; 6. the sorting the identifications by their scores. The user/operator may also choose search parameters that affect the list of reference data sets, for example, 1. taxonomical identification of the microorganism; 2. identification number; 3. protein name; 4. text notes of the references.

Second, the primary keys (an integer that uniquely identifies a dataset) of the datasets are stored in random access memory (RAM) and looped through and their respective data to be individually compared against the user/operator selected dataset iteratively. Both datasets, the one chosen by the user/operator to run for a comparison and the current iteration for comparison against the whole database, are "filtered" by the parameters selected by the user/operator as described above. This is then placed into two separate memory tables to be compared against one another. Memory table is a term being used to describe a MySQL DB table that utilizes the memory based storage engine (e.g. RAM). This increases the speed of the comparison.

4. USDAα Peak Matching Algorithm

The USDA peak matching algorithm counts the total number of in silico fragment ions and adds this number to the total number of MS/MS fragment ions whose intensity is equal to or greater than the minimum intensity threshold.

The algorithm then counts the total number of in silico fragment ions that are within Δm/z of MS/MS fragment ions, i.e. the number of "matches" between two datasets. The number of counted "matches" is multiplied by two and divided by the previously mentioned summation of in silico MS/MS and MS/MS fragment ions. This number is then multiplied by 100% to give the USDA peak matching score. The USDA peak matching score has a theoretical range from 0 to 100% with 0% meaning no matches were identified and 100% meaning every single peak was matched between the two datasets. A non-zero Δm/z means that it is possible for an MS/MS fragment ion peak to "match" to two (or more) in silico fragment ion peaks (or vice versa). Such "multiple" matches are counted only once by the USDA peak matching algorithm, otherwise a USDA peak matching score greater than 100% may occur. This counting/matching/scoring process is identical to the method used for comparing two MS spectra of MALDI-TOF MS data.

5. USDAβ Peak Matching Algorithm

The peak matching algorithm involves counting the number of MS/MS fragment ions whose intensity is equal to or greater than a relative intensity threshold (e.g. 2%). The algorithm then counts the number of in silico fragment ions whose m/z falls within a specified m/z tolerance (e.g. ±2.5 Th) to that of the m/z of MS/MS fragment ions, i.e. counting the number of "peak matches" between MS/MS fragment ions and in silico fragment ions of the two datasets. The number of "peak matches" is then divided by the total number of MS/MS fragment ions above the specified intensity threshold. This number is then multiplied by 100% to give the peak matching score shown below:

$$USDA\beta \text{ Score} = 100 \times \frac{\text{Number of peak matches}}{\text{(Number of } MS/MS \text{ fragment ion peaks)}}$$

The USDAβ peak matching score has a theoretical range from 0 to 100%. Zero percent indicates no peak matches were identified and 100% indicates every single MS/MS fragment ion was matched to an in silico fragment ion of an identification. A non-zero fragment ion m/z tolerance indicates that it is possible for an MS/MS fragment ion m/z to "match" to the m/z of two (or more) in silico fragment ions (or vice versa). Such multiple matches are counted only once by the algorithm, otherwise a score greater than 100% may result. The highest scoring protein/microorganism identification that is significantly higher than the second highest scoring protein/microorganism identification constitutes a presumptive correct identification. "Significantly" as used herein refers a relative difference in score between the top identification and the second highest scoring identification, typically of about 15-20% (or greater).

Software functionality allows selective operation of one or the other algorithms (or both). Algorithm computation time is provided by the software. In addition, the protein/microorganism identifications can be "ranked" by either the peak matching scores or p-values.

6. Computation Speed of USDA Algorithms

The USDA peak matching algorithms are less computationally complex than other protein identification algorithms known in the art e.g., a p-value calculation (see e.g., Demirev et al. (2005) supra). Thus, the computation time of the USDA peak matching algorithms are rapid as well as accurate. Indeed, in an exemplary embodiment, computation time is as much as 50% faster than the same p-value calculation. As the number of in silico bacterial proteins increase due to the increasing number of bacterial genomes, algorithm computation time plays an increasingly important factor in rapid and efficient protein/microorganism identification.

The following examples are offered to illustrate, but not to limit the invention.

EXAMPLES

Example 1

The following example illustrates an exemplary microorganism identification protocol for the identification of a microorganism using matrix assisted laser desorption ionization (MALDI) mass spectrometry to identify an unknown protein and it corresponding source organism.

Flow Chart of Protein/Microorganism Identification

A 1 μL loop of bacterial cells suspended in 0.5 mL of solution (33% CH₃CN, 67% H₂O and 0.1% TFA). Bead-beating 60 seconds, centrifugation 5 minutes @ 10,000 rpm.

↓

A 0.5 μL aliquot of supernatant is deposited onto stainless steel target pre-spotted with MALDI matrix.

↓

Collect MS and MS/MS data of bacterial strain using MALDI tandem mass spectrometer (e.g. MALDI-TOF-TOF).

↓

Raw MS and MS/MS data is processed and converted to ASCII formatted mass-to-charge (m/z) vs. intensity data. The ASCII formatted MS and MS/MS data are uploaded to their respective MySQL MS database (DB) and MySQL MS/MS DB of the USDA software.

↓

From the ExPASy TagIdent web server, a search/retrieve/download was conducted of all bacterial proteins with a molecular weight (MW) equivalent in mass to the protein precursor ion m/z (PPI m/z) after removal of its proton (-1 Th) and within a pre-set mass tolerance, e.g. MW = (PPI m/z - 1) ± 5 Da.

↓

-continued

From the ExPASy TagIdent web server, a search/retrieve/download was conducted of all bacterial proteins with a MW equivalent in mass to the PPI m/z after removal of its proton (-1 Th) and addition of the mass of a methionine residue (+131 Da) and within a pre-set mass tolerance, e.g. MW = [(PPI m/z - 1) + 5 Da.

The MW = (PPI m/z - 1) ± 5 Da and the MW = [(PPI m/z - 1) + 131] ± 5 Da searches generate two large Fasta files each containing ~600-700 bacterial protein sequences.

The MW = (PPI m/z - 1) + 131] ± 5 Da Fasta file is edited to remove N-terminal methionine from all protein amino acid sequences. The protein identification is also modified to highlight this in silico post-translational modification (PTM).

Each multi-sequence Fasta file is processed using a beta-version of the commercial software GPMAW. The beta-version (8.01a5) has enhanced features developed by ©Lighthouse Data at USDA's request.

Each processed FASTA file generates ~ 600-700 text files. Each text files. Each text file contains the taxonomic identification of the microorganism, the protein identification and its MW (average) and its in silico fragment ions as identified by their m/z (average), their ion type (a, b, b-18, y, y-17, y-18) and the two amino acid residues immediately adjacent to the site of polypeptide backbone cleavage which generated the specific fragment ion.

The MW = (PPI m/z - 1) ± 5 Da text files are sorted by file size in order to identify any proteins having a putative signal peptide (SP). These SP-associated text files are excluded from upload to the MySQL In Silico DB. Instead the SP-identified proteins are individually downloaded from the ExPASy web server as single sequence FASTA files. These single sequence FASTA files are edited to remove the SP, and the protein identification is modified to highlight this in silico post-translational modification (PTM). These new sequences are compiled into a single FASTA file and processed by GPMAW. The text files generated are then ready for upload to the MySQL In Silico DB.

The MW = [(PPI m/z - 1) + 131] ± 5 Da text files are sorted by file size in order to identify a small number of proteins having a putative SP. These SP-associated text files are excluded from upload to the MySQL In Silico DB. The non-SP-associated text files are ready for upload to the MySQL In Silico DB.

In silico text files are batch uploaded to the MySQL In Silico DB using a Java client (i.e. a binary file [jar file] that is interpreted by the Java Runtime Environment or JRE) that is part of, but separate from, the USDA software.

A "MS/MS To In Silico Comparison" functionality of the USDA software compares the MS/MS spectrum against all in silico MS/MS spectra whose calculated protein MW falls within the pre-specified protein MW tolerance of the PPI m/z, e.g. MW = (PPI m/z - 1) ± 5 Da.

Protein/bacteria IDs are sorted and displayed on the basis of their USDA score (α or β) and/or p-value.

-continued

Protein/bacteria IDs are also confirmed by plots of fragment ion error analysis: systematic error (i.e. instrument calibration error) versus random error.

Protein/bacteria IDs are also confirmed by residue-specific fragment ions, e.g. the number and percentage of D,E,P-specific fragments ions.

Example 2

The following example illustrates an exemplary method for bacterial protein extraction for MALDI-TOF/TOF analysis.

Bacterial proteins were extracted from *Campylobacter* cells using a technique that has been previously reported (see e.g., Mandrell R E, et al. *Applied Environ. Microbio.* 2005; 71: 6292; Fagerquist C K, et al. *Anal. Chem.* 2005; 77: 4897; Fagerquist C K, et al. *J. Proteome Research.* 2006; 5: 2527. Briefly, *C. jejuni* (strain RM1221), *C. coli* (strain RM2228), *C. upsaliensis* (strain RM3195) and *C. lari* (strain RM2100) were each cultured on non-selective growth media for 24-48 hours. One μL of cells were transferred to a microcentrifuge tube containing 0.5 mL of extraction solvents (67% water, 33% acetonitrile and 0.1% TFA) and 40 mg of 0.1 mm zirconia/silica beads (BioSpec Products Inc., Bartlesville, Okla.). The tube was capped and agitated for 60 seconds with a bead-beater. The tube was then centrifuged at 10,000 rpm for 4-5 minutes. An equal volume of sample supernatant was combined with an equal volume of either α-cyano-4-hydroxycinnamic acid (CCA) or sinapinic acid, mixed and spotted onto a 384-spot stainless steel plate. Samples were allowed to air-dry prior to analysis.

Example 3

The following example illustrates an exemplary mass analysis using high energy collision-induced dissociation as well as post-source dissociation on a MALDI tandem-TOF mass spectrometer to generate MS/MS spectra in reflectron-mode in positive ion mode.

Samples were analyzed using an Applied Biosystems 4800 TOF-TOF™ Analyzer mass spectrometer (Foster City, Calif.). Spectra were analyzed in both MS linear-mode and MS/MS in reflectron-mode in positive ion mode. Source acceleration in the first source in linear-mode was 20.00 kV. In MS/MS reflectron-mode, ions were initially accelerated at 8.00 kV in the first source, mass-selected with a timed ion selector, the mass-selected ions were then decelerated to 1.70 kV, fragmented with the target gas (air) in the floating collision cell at 2 kV and the fragment ions formed were re-accelerated to 15 kV in the second source. Data was collected with the metastable (precursor ion) suppressor, located after the 2nd source, in both "on" and "off" mode. A two-stage reflectron mirror assembly was operated at 10.910 kV (mirror 1) at 18.750 kV (mirror 2). Both linear and reflectron detectors were operated at 2.190 kV. Linear data were externally calibrated using insulin (MW=5734.59 Da), thioredoxin (MW=111674.48 Da) and apomyoglobin (MW=16,952.56 Da). Reflectron-TOF MS/MS spectra were calibrated using updated instrument default calibration.

MS and MS/MS data were analyzed using the commercially available instrument software (Data Explorer Software®, Version 4.9). MS data were processed using a noise filter (correlation factor=0.7). MS/MS data were processed first with an advanced baseline correction (peak width=32, flexibility=0.5, degree=0.1), then with noise removal (standard deviations=2) and finally with a Gaussian smooth (filter width=31).

Example 4

The intact protein biomarker, thioredoxin from *Campylobacter upsaliensis* strain RM3195 was mass-selected and fragmented in the gas phase using a MALDI-TOF-TOF mass spectrometer by methods known in the art (see e.g., Example 3 above). The protein was identified previously by "bottom-up" proteomics techniques (see e.g., Fagerquist, C. K. *J. Proteome Research.* 2007; 6: 2539-2549). Since the identity of the proteins had been determined previously, it served as a control protein for confirmation of the accuracy and rapidity of identification achievable by the method for identification of an unknown protein disclosed herein.

The sequence-specific fragment ions generated were used to identify the protein (and thus the microorganism) by comparison against a database containing in silico fragment ions derived from protein sequences from bacterial genomic databases.

The USDA peak-matching algorithm alpha ($\alpha$) which has the formula:

$$\text{USDA}\alpha \text{ Score} = 100 \times \frac{2 \times (\text{Number of peak matches})}{\begin{array}{c}(\text{Number of peaks in the mass spectrum of}\\ \text{the unknown protein} + \\ \text{Number of peaks in the mass spectrum of} \\ \text{known protein sequences})\end{array}}$$

was incorporated into the data analysis software as disclosed herein and was used to score/rank protein/microorganism identifications. The algorithm correctly identified the thioredoxin protein biomarker from nearly ~1400 possible bacterial proteins. The algorithm also gave comparable rankings in protein identifications as that obtained with a much more complicated p-value calculation (see e.g., Demirev et al. (2005) *Anal Chem* 77:7455).

Protein identifications made using the USDA peak-matching mathematical algorithm were confirmed by error analysis as disclosed herein and also by residue specific analysis. As is illustrated below, the correctly identified protein exhibits only systematic error that is due to the inherent calibration error of the mass analyzer, whereas incorrect identifications exhibit random error caused by false "matches". Furthermore, correct identification is confirmed by residue specific analysis. Correct identifications as confirmed by residue specific analysis reveal an increase in the absolute value of the highest USDA peak matching score, as well as an increase in the difference between the highest USDA peak matching score and the second highest USDA peak matching score.

Example 5

The following example illustrates that a correct protein identification made using the peak-matching mathematical algorithm disclosed herein is confirmed by analysis of the difference in m/z between the MS/MS fragment ions of the protein and their putative "matches" from a MS/MS in silico spectra. For a correct identification, of thioredoxin protein, a linear regression analysis fit of the data reveals only systematic error which is due to the inherent calibration error of the mass analyzer (see e.g., FIG. 9). In contrast, a linear regression analysis fit of the data for an incorrect identification of the protein thioredoxin exhibits random error caused by false "matches" (see e.g., FIG. 10).

Figure 4:
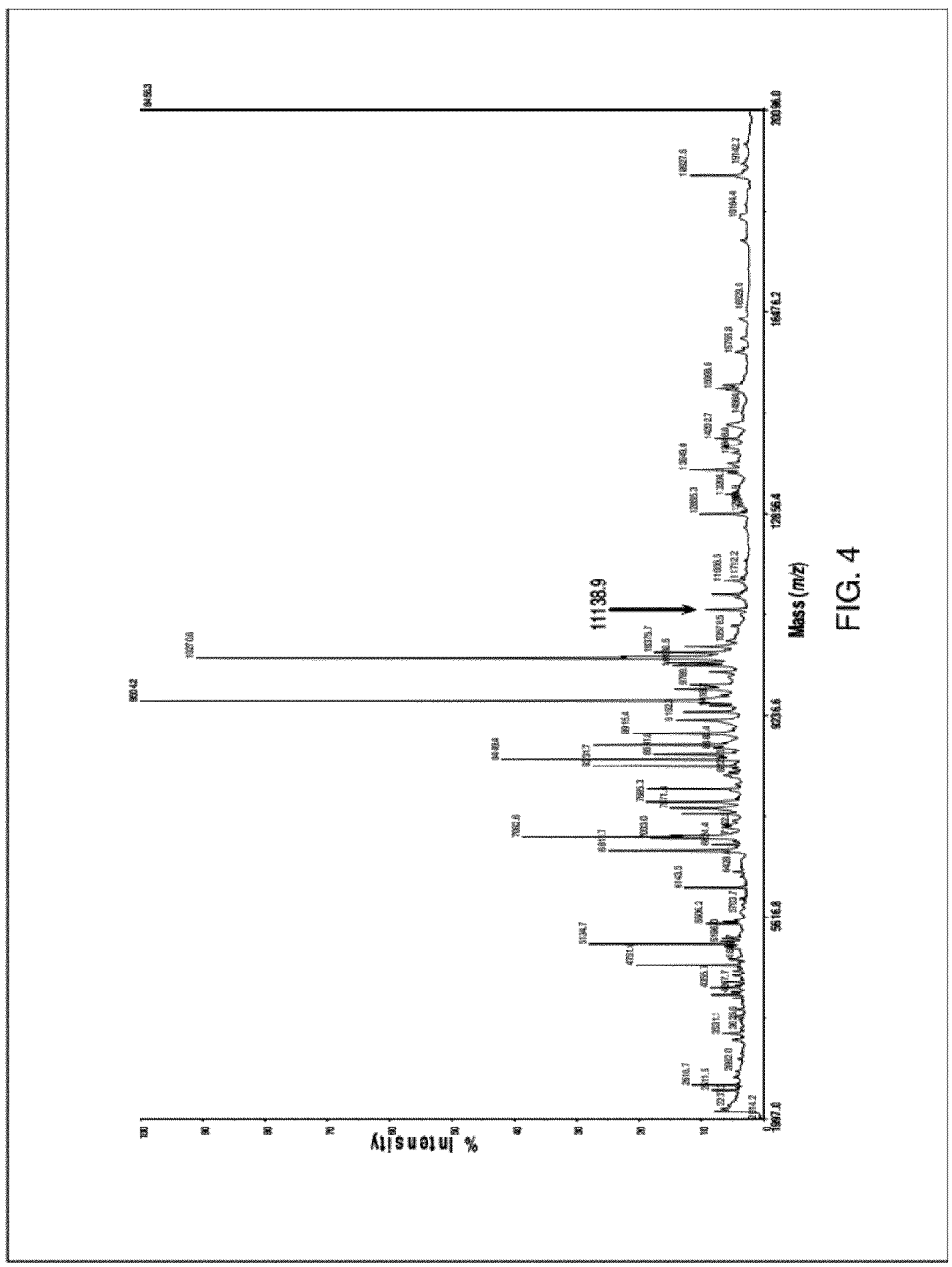
FIG. 4 shows an MS spectrum (as displayed in the MALDI-TOF-TOF instrument software) of the extracted cell lysate of *Campylobacter upsaliensis* (strain RM3195) analyzed by MALDI-TOF-MS using sinapinic acid as the MALDI matrix.

FIG. 4 shows an MS spectrum (as displayed in the MALDI-TOF-TOF instrument software) of the extracted cell lysate of *Campylobacter upsaliensis* (strain RM3195) analyzed by MALDI-TOF-MS using sinapinic acid as the MALDI matrix. The protein biomarker ion at m/z 11138.9 was analyzed by tandem mass spectrometry. The MS/MS spectrum of protein biomarker ion at m/z 11138.9 is shown in FIG. 5.

Figure 5:
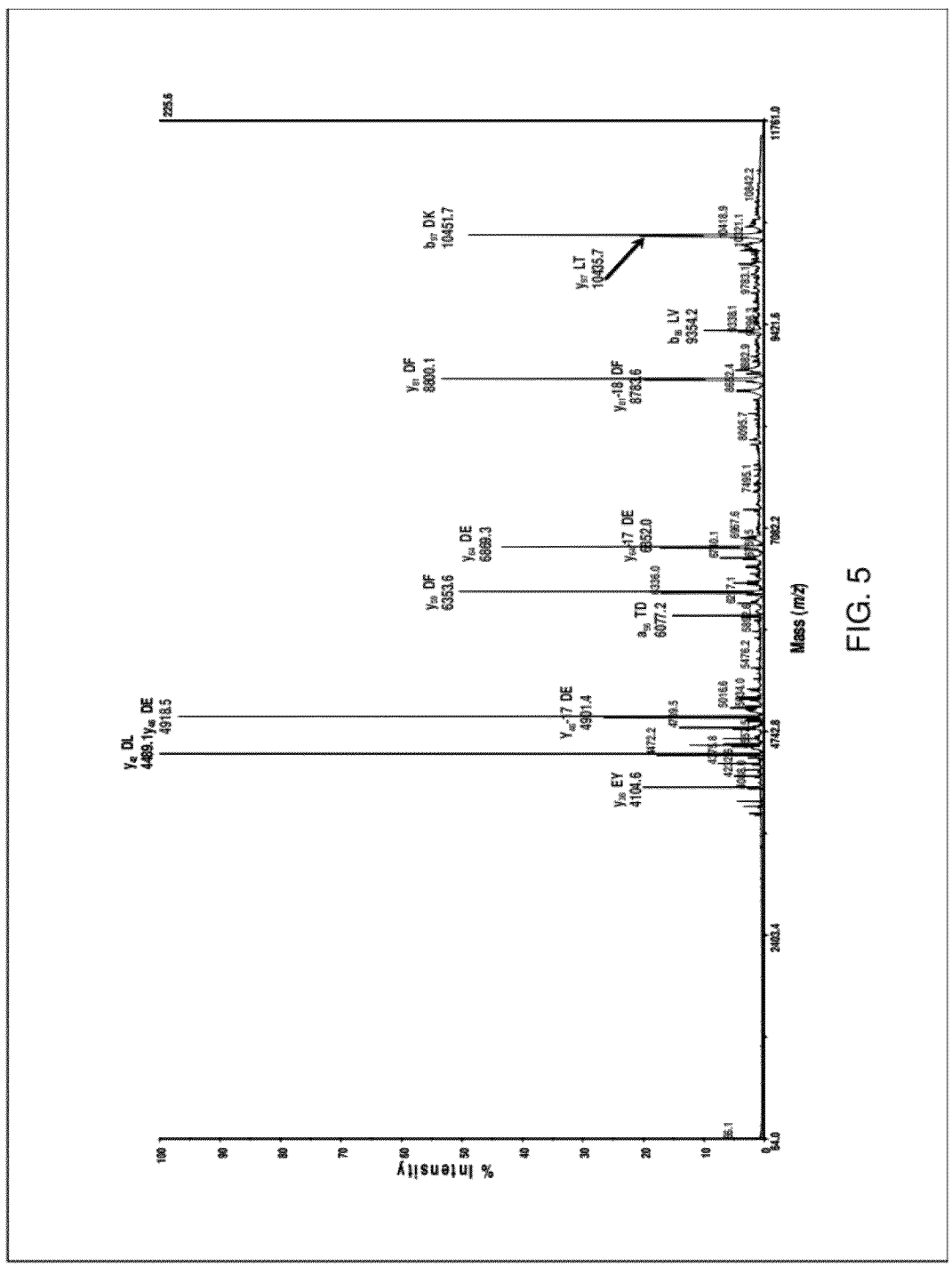
FIG. 5 shows the MS/MS spectrum (as displayed in the MALDI-TOF-TOF instrument software) of the protein biomarker ion of *Campylobacter upsaliensis* (strain RM3195) at m/z 11138.9 analyzed on a MALDI-TOF-TOF-MS using sinapinic acid as the MALDI matrix.

FIG. 5 shows the MS/MS spectrum (as displayed in the MALDI-TOF-TOF instrument software) of the protein biomarker ion of *Campylobacter upsaliensis* (strain RM3195) at m/z 11138.9 analyzed on a MALDI-TOF-TOF-MS using sinapinic acid as the MALDI matrix. Prominent fragment ions are identified by their m/z, ion type and number and amino acid residues immediately adjacent to the site of polypeptide backbone cleavage giving rise to the fragment ion. As can be seen, most (if not all) of the fragment ions are the result of polypeptide backbone cleavage immediately adjacent to a D (aspartic acid) or E (glutamic acid) residues. This MS/MS data is then centroided (i.e. converted to ASCII format: m/z vs. absolute intensity) and exported for uploading to the USDA software.

Figure 6:
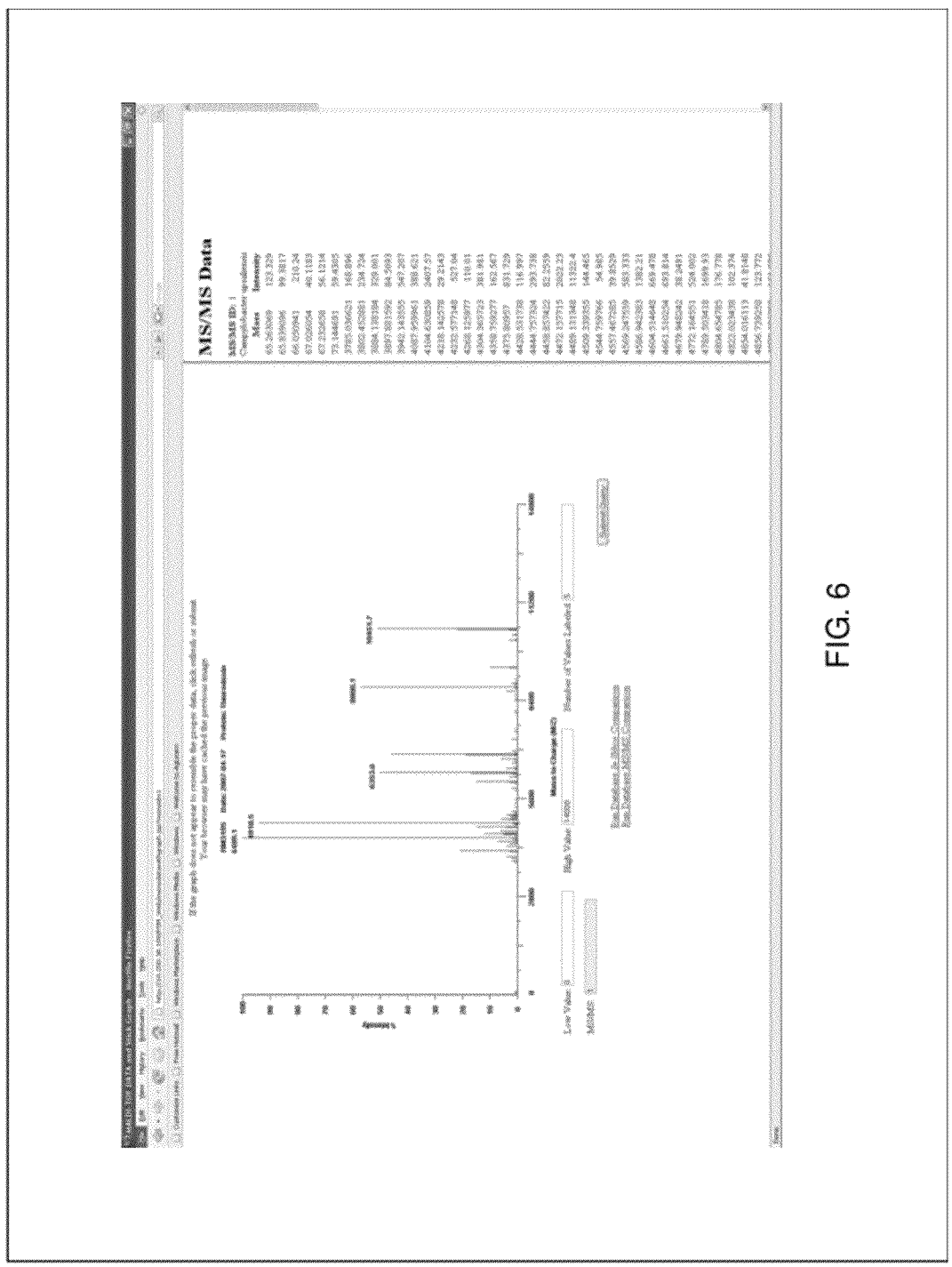
FIG. 6 shows an ASCII MS/MS spectrum (m/z vs. relative intensity as displayed in the USDA software window) of thioredoxin from *Campylobacter upsaliensis* (strain RM3195) previously displayed in FIG. 5. The MS/MS data in FIG. 5 was centroided (i.e. converted to ASCII format: m/z vs. absolute intensity), exported from the MALDI-TOF-TOF instrument software and imported to the MS/MS databases of the USDA software. The m/z and absolute intensity of MS/MS fragment ions are shown in the sidebar.

FIG. 6 shows an ASCII MS/MS spectrum (m/z vs. relative intensity as displayed in the USDA software window) of thioredoxin from *Campylobacter upsaliensis* (strain RM3195) previously displayed in FIG. 5. The MS/MS data in FIG. 5 was centroided (i.e. converted to ASCII format: m/z vs. absolute intensity), exported from the MALDI-TOF-TOF instrument software and imported to the MS/MS databases of the USDA software. The m/z and absolute intensity of MS/MS fragment ions are shown in the sidebar.

Figure 7:
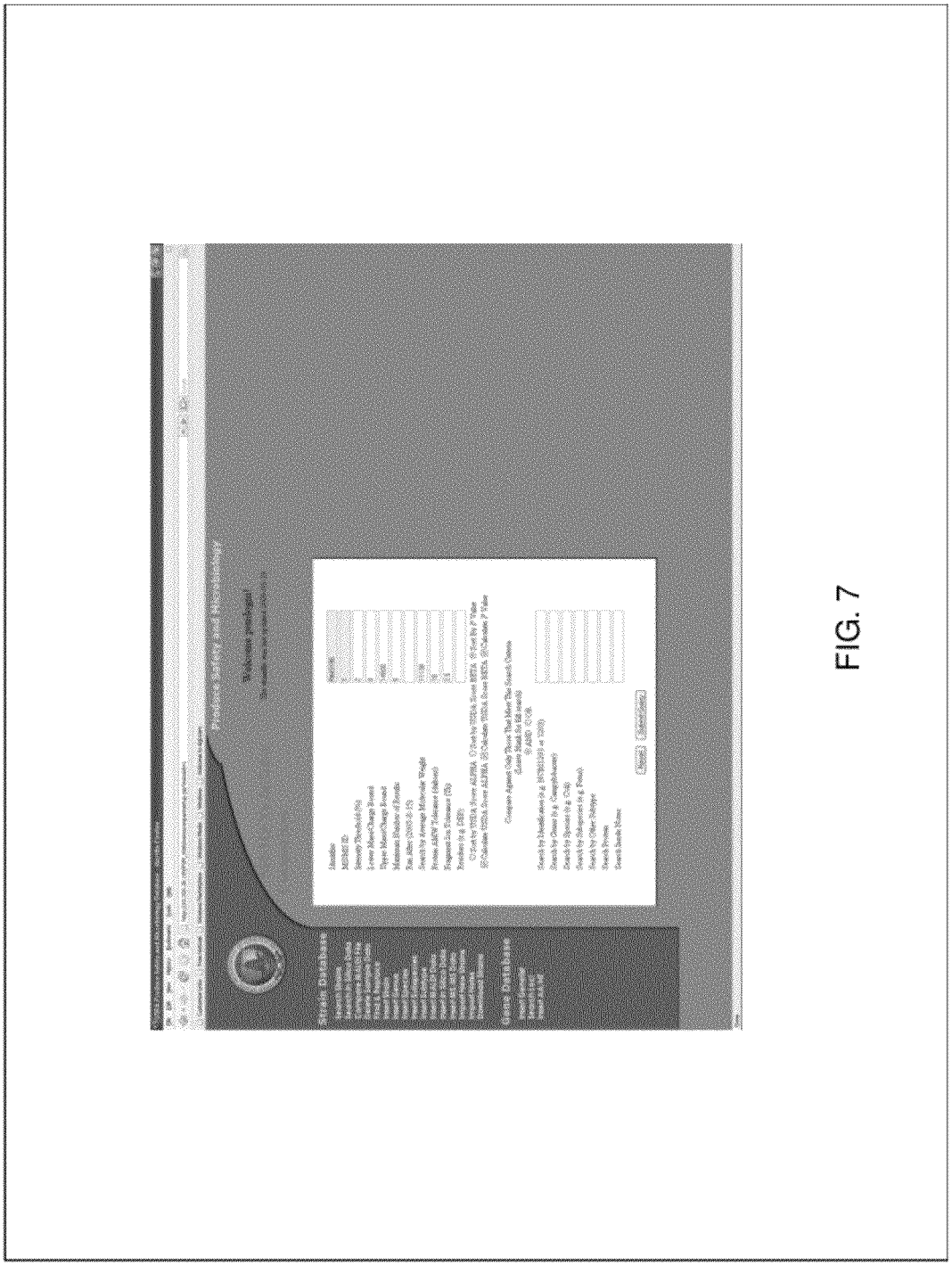
FIG. 7 shows the "MS/MS To In Silico Comparison" search parameter table as displayed in the USDA software window.

FIG. 7 shows The "MS/MS To In Silico Comparison" search parameter table as displayed in the USDA mass spectrometry comparison software window. The user/operator defines the m/z range to be compared, the number of results to be displayed, the average molecular weight of the protein to be searched (with an associated molecular weight tolerance, e.g. ±10 Da), the fragment ion m/z tolerance (in Th) and restrictions (if any) on residue-specific fragment ions, i.e. fragment ions generated from polypeptide cleavage immediately adjacent to specific amino acid residues. The absence of an entry in the "Residues" field indicates that all fragment ions generated from the polypeptide (protein) are to be included in the search. The user/operator can also select which scoring algorithm to use for analysis, i.e. USDA peak matching algorithm or the p-value algorithm (or both). The scores/identifications can also be ranked/sorted.

FIG. 8 shows the in silico MS/MS spectrum (as displayed in the USDA software window) of the protein thioredoxin of *Campylobacter upsaliensis* (strain RM3195). The in silico sequence was post-translationally modified (PTM) to remove the N-terminal methionine. In silico fragment ions m/z are shown in the sidebar.

Table 1A (below) displays the top five identifications of a protein biomarker of *Campylobacter upsaliensis* (strain RM3195) at m/z 11138.9 (as shown in FIG. 4) and analyzed by MS/MS using MALDI-TOF-TOF mass spectrometry (as shown in FIG. 5 and FIG. 6) and compared to all in silico MS/MS fragment ions of bacterial protein sequences having the same molecular weight as the biomarker (within ±5 Da. This corresponded to 1409 in silico protein sequences). Table 1A compares peak matching scores obtained using the USDAα peak matching algorithm to the p-value calculation known in the art. The protein biomarker had been identified previously by "bottom-up" proteomics techniques as thioredoxin (Fagerquist, C. K., 2007, *J. Proteome Res.*, 6, 2539-2549). The top identification correctly identifies the protein biomarker and its source microorganism.

TABLE 1A

| In Silico ID | Identifier | Sample Name | Protein | USDA Score-α | P-value |
|---|---|---|---|---|---|
| 7653 | >Q4HNM5|Q4HNM5_CAMUP | Campylobacter upsaliensis RM3195. | Thioredoxin PTM_Met 11136.76 | 12.95 | 7.7E−19 |
| 6714 | >B1WRD3|B1WRD3_CYAA5 | Cyanothece (strain ATCC 51142). | Carbon dioxide concentrating mechanism protein 11133.85 | 8.43 | 3.6E−6 |
| 6462 | >A4T659|A4T659_MYCGI | Mycobacterium gilvum (strain PYR_GCK) (Mycobacterium flavescens (strain ATCC 700033/PYR_GCK)). | Putative uncharacterized protein 11142.24 | 7.36 | 3.1E−4 |
| 7088 | >Q1LMQ8|Q1LMQ8_RALME | Ralstonia metallidurans (strain CH34/ATCC 43123/DSM 2839). | Putative uncharacterized protein PTM_23SigPep 11128.81 | 6.93 | 1.1E−3 |
| 7545 | >Q18XI2|Q18XI2_DESHD | Desulfitobacterium hafniense (strain DCB_2). | Small multidrug resistance protein PTM_Met 11138.67 | 6.74 | 1.6E−3 |

MS/MS to In silico Comparison Parameters
Intensity threshold: 2%
m/z range for comparison: 0-14,000 Th.
Fragment ion tolerance: 2.5 Th.
Protein MW 11138 ± 10 Da.
ALL in silico fragment ions compared.
"PTM_Met" indicates that the in silico protein sequence was modified to remove the N-terminal methionine.
"PTM_#SigPep" indicates that the in silico protein sequence was modified to remove a signal peptide.
Algorithm Computation Speeds
USDA peak matching algorithm alpha: 33.8 seconds.
P-value calculation: 47.1 seconds.

Table 1B (below) displays the top five identifications of the same protein biomarker of *Campylobacter upsaliensis* (strain RM3195) at m/z 11138.9 (as shown in FIG. 4) and analyzed by MS/MS using MALDI-TOF-TOF mass spectrometry (as shown in FIG. 5 and FIG. 6) and compared to all 1409 in silico MS/MS fragment ions of bacterial protein sequences having the same molecular weight as the biomarker (within ±5 Da). Table 1B compares peak matching scores obtained using the USDAβ peak matching algorithm to the p-value calculation known in the art.

Figure 9:
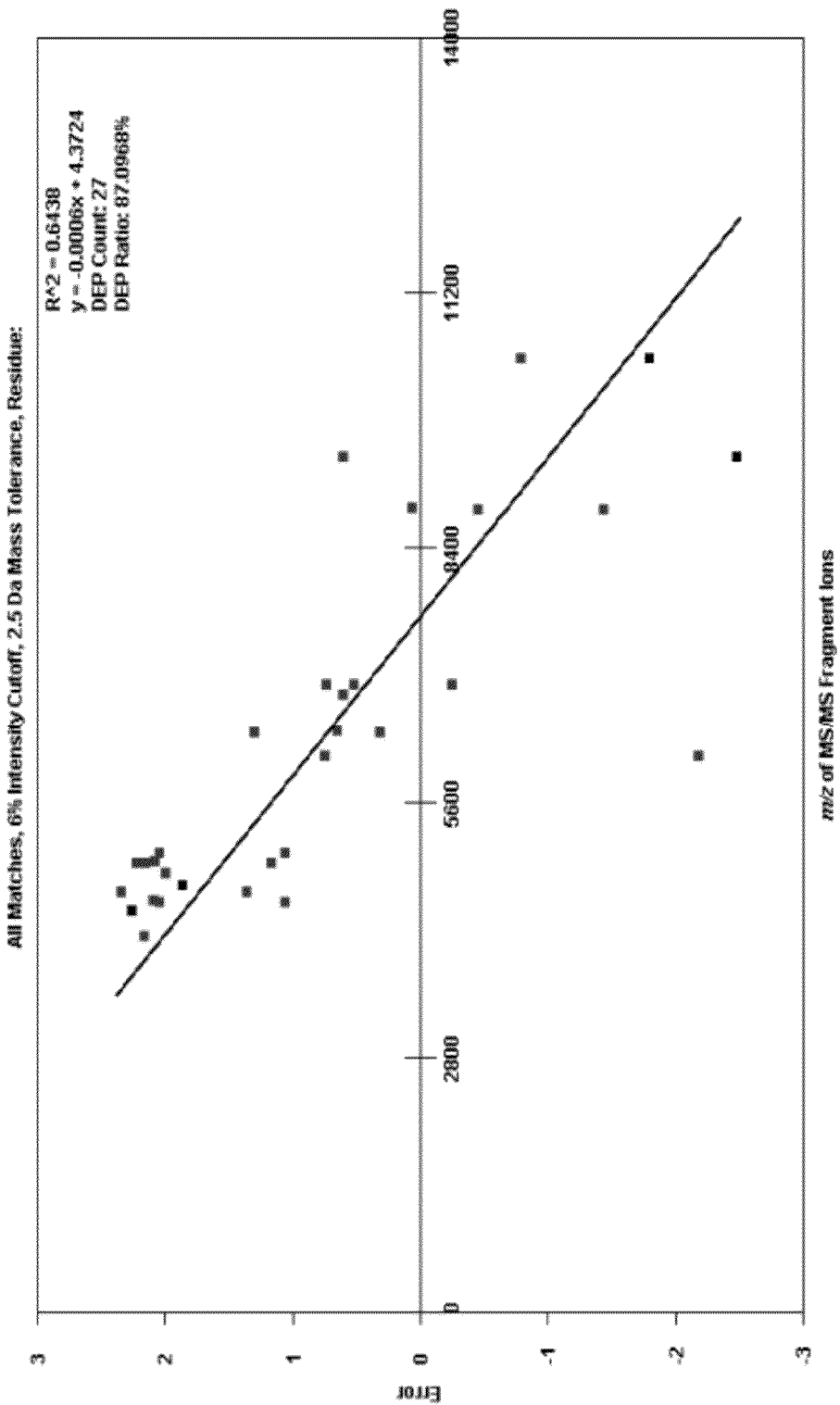
FIG. 9 shows a plot of fragment ion error (as displayed in the USDA software) as a function of the MS/MS fragment ion mass-to-charge (m/z) of the protein biomarker thioredoxin (from *Campylobacter upsaliensis* strain RM3195) and its "match" to the in silico fragment ions of thioredoxin of *Campylobacter upsaliensis* strain RM3195 (the highest scoring identification and the correct identification). Fragment ion error (Δm/z) is the difference between m/z of an MS/MS fragment ion and the m/z of its putative in silico fragment ion "match". A red square represents a "match" whose in silico fragment ion was generated from a protein backbone cleavage site that is adjacent to a D, E or P residue. A black square represents a "match" whose in silico fragment ion was generated from a protein backbone cleavage site that is adjacent to only non-D,E,P residues.

FIG. 9 shows a plot of fragment ion error (as displayed in the USDA software) as a function of the MS/MS fragment ion mass-to-charge (m/z) of the protein biomarker thioredoxin (from *Campylobacter upsaliensis* strain RM3195) and its "match" to the in silico fragment ions of thioredoxin of *Campylobacter upsaliensis* strain RM3195 (the highest scoring identification and the correct identification). Fragment ion error (Δm/z) is defined here as the difference between m/z of an MS/MS fragment ion and the m/z of its putative in silico fragment ion "match". A red square represents a "match"

TABLE 1B

| In Silico ID | Identifier | Sample Name | Protein | USDA Score-β | P-value |
|---|---|---|---|---|---|
| 1262 | >Q4HNM5|Q4HNM5_CAMUP | Campylobacter upsaliensis RM3195. | Thioredoxin PTM_Met 11136.76 | 82.69 | 7.7E−19 |
| 323 | >B1WRD3|B1WRD3_CYAA5 | Cyanothece (strain ATCC 51142). | Carbon dioxide concentrating mechanism protein 11133.85 | 53.85 | 3.6E−6 |
| 71 | >A4T659|A4T659_MYCGI | Mycobacterium gilvum (strain PYR-GCK) (Mycobacterium flavescens (strain ATCC 700033/PYR-GCK)). | Putative uncharacterized protein 11142.24 | 46.15 | 3.1E−4 |
| 697 | >Q1LMQ8|Q1LMQ8_RALME | Ralstonia metallidurans (strain CH34/ATCC 43123/DSM 2839). | Putative uncharacterized protein PTM_23SigPep 11128.81 | 44.23 | 1.1E−3 |
| 1154 | >Q18XI2|Q18XI2_DESHD | Desulfitobacterium hafniense (strain DCB-2). | Small multidrug resistance protein PTM_Met 11138.67 | 44.23 | 1.6E−3 |

MS/MS to In silico Comparison Parameters
Intensity threshold: 2%
m/z range for comparison: 0-14,000 Th.
Fragment ion tolerance: 2.5 Th.
Protein MW 11138 ± 10 Da.
ALL in silico fragment ions compared.
"PTM_Met" indicates that the in silico protein sequence was modified to remove the N-terminal methionine.
"PTM_#SigPep" indicates that the in silico protein sequence was modified to remove a signal peptide.
Algorithm Computation Speeds
USDA peak matching algorithm beta: 35.0 seconds.
P-value calculation: 48.4 seconds.

whose in silico fragment ion was generated from a protein backbone cleavage site that is adjacent to a D, E or P residue. A black square represents a "match" whose in silico fragment ion was generated from a protein backbone cleavage site that is adjacent to only non-D,E,P residues. Note the high number (27) and percentage (87.1%) of "matches" that are associated with D,E,P residues supporting the correctness of the identification. A linear regression fit of the data indicates a correlation ($R^2$=0.6438) between $\Delta m/z$ and MS/MS fragment ion m/z due to systematic error caused by calibration error of the mass analyzer. This systematic error confirms that this is a correct identification.

Figure 10:
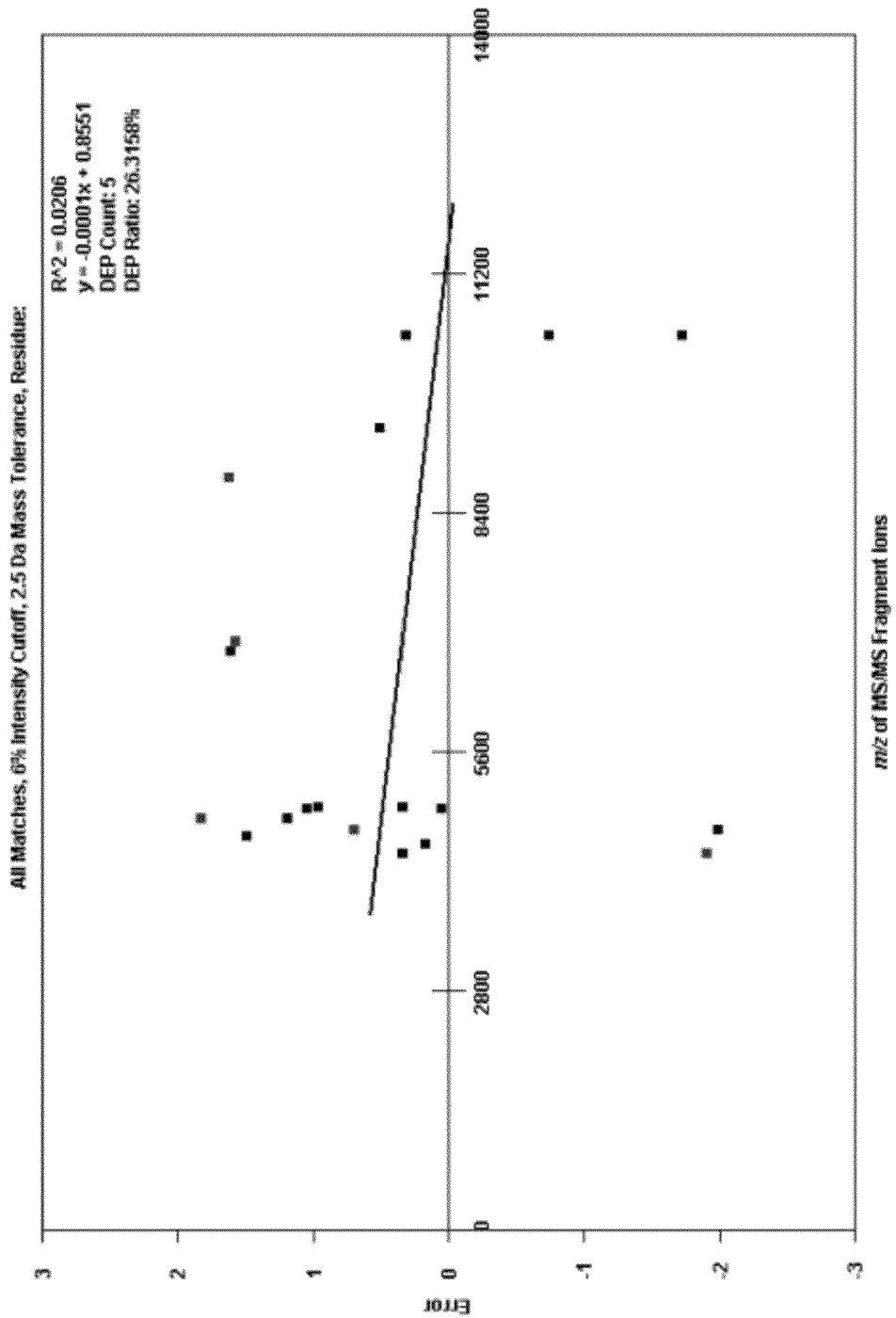
FIG. 10 shows a plot of fragment ion error (as displayed in the USDA software) as a function of the MS/MS fragment ion mass-to-charge (m/z) of the protein biomarker thioredoxin (from *Campylobacter upsaliensis* strain RM3195) and its "match" to the in silico fragment ions of carbon dioxide concentrating mechanism protein of *Cyanothece* strain ATCC 51142 (the second highest scoring identification and an incorrect identification). Fragment ion error (Δm/z) is defined here as the difference between m/z of an MS/MS fragment ion and the m/z of its putative in silico fragment ion "match". A red square represents a "match" whose in silico fragment ion was generated from a protein backbone cleavage site that is adjacent to a D, E or P residue. A black square represents a "match" whose in silico fragment ion was generated from a protein backbone cleavage site that is adjacent to only non-D,E,P residues.

FIG. 10 shows plot of fragment ion error (as displayed in the USDA software) as a function of the MS/MS fragment ion mass-to-charge (m/z) of the protein biomarker thioredoxin (from *Campylobacter upsaliensis* strain RM3195) and its "match" to the in silico fragment ions of carbon dioxide concentrating mechanism protein of *Cyanothece* strain ATCC 51142 (the second highest scoring identification and an incorrect identification). Fragment ion error ($\Delta m/z$) is defined here as the difference between m/z of an MS/MS fragment ion and the m/z of its putative in silico fragment ion "match". A red square represents a "match" whose in silico fragment ion was generated from a protein backbone cleavage site that is adjacent to a D, E or P residue. A black square represents a "match" whose in silico fragment ion was generated from a protein backbone cleavage site that is adjacent to only non-D,E,P residues. Note the low number (5) and percentage (26.3%) of "matches" that are D,E,P-associated supporting that this is not the correct identification. A linear regression fit of the data indicates a very poor correlation ($R^2$=0.0206) between $\Delta m/z$ and MS/MS fragment ion m/z, i.e. random statistical error. This random error supports that this is an incorrect identification.

Table 1C (below) displays the top five identifications of a protein biomarker of *Campylobacter upsaliensis* (strain RM3195) at m/z 11138.9 (as shown in FIG. 4) and analyzed by MS/MS using MALDI-TOF-TOF mass spectrometry (as shown in FIG. 5 and FIG. 6) compared to D,E,P-specific in silico MS/MS fragment ions of bacterial protein sequences having the same molecular weight as the biomarker (within ±5 Da). This corresponded to 1409 in silico protein sequences. The protein biomarker had been identified previously by "bottom-up" proteomics techniques as thioredoxin (Fagerquist, C. K., 2007, *J. Proteome Res.*, 6, 2539-2549). The top identification correctly identifies the protein biomarker and its source microorganism. Table 1C compares peak matching scores obtained using the USDAα peak matching algorithm to the p-value calculation known in the art.

TABLE 1C

| In Silico ID | Identifier | Sample Name | Protein | USDA Score-α | P-value |
|---|---|---|---|---|---|
| 7653 | >Q4HNM5\|Q4HNM5_CAMUP | *Campylobacter upsaliensis* RM3195. | Thioredoxin PTM_Met 11136.76 | 25.00 | 3.0E−21 |
| 7333 | >A8LX75\|A8LX75_SALAI | *Salinira arenicola* (strain CNS_205). | Putative uncharacterized protein PTM_Met 11140.56 | 12.99 | 9.0E−5 |
| 6534 | >A7A905\|A7A905_BIFAD | *Bifidobacterium adolescentis* L2_32. | Putative uncharacterized protein 11134.94 | 11.50 | 9.4E−5 |
| 6527 | >A6QD71\|A6QD71_STAAE | *Staphylococcus aureus* (strain Newman). | Putative uncharacterized protein 11138.98 | 11.54 | 1.5E−4 |
| 6840 | >Q2G1R1\|Q2G1R1_STAA8 | *Staphylococcus aureus* (strain NCTC 8325). | Putative uncharacterized protein 11138.98 | 11.54 | 1.5E−4 |

MS/MS to In silico Comparison Parameters
Intensity threshold: 2%
m/z range for comparison: 0-14,000 Th.
Fragment ion tolerance: 2.5 Th.
Protein MW 11138 ± 10 Da.
D,E,P-specific in silico fragment ions compared.
"PTM_Met" indicates that the in silico protein sequence was modified to remove the N-terminal methionine.
"PTM_#SigPep" indicates that the in silico protein sequence was modified to remove a signal peptide.
Algorithm computation speeds
USDA peak matching algorithm alpha: 16.1 seconds.
P-value calculation: 37.1 seconds.

Table 1D (below) displays the top five identifications of the same protein biomarker as in Table 1C of *Campylobacter upsaliensis* (strain RM3195) at m/z 11138.9 (as shown in FIG. 4) and analyzed by MS/MS using MALDI-TOF-TOF mass spectrometry (as shown in FIG. 5 and FIG. 6) compared to D,E,P-specific in silico MS/MS fragment ions of bacterial protein sequences having the same molecular weight as the biomarker (within ±5 Da). This corresponded to 1409 in silico protein sequences. The protein biomarker had been identified previously by "bottom-up" proteomics techniques as thioredoxin (Fagerquist, C. K., 2007, *J. Proteome Res.*, 6, 2539-2549). The top identification correctly identifies the protein biomarker and its source microorganism. Table 1D compares peak matching scores obtained using the USDAβ peak matching algorithm to the p-value calculation known in the art.

TABLE 1D

| In Silico ID | Identifier | Sample Name | Protein | USDA Score-β | P-value |
|---|---|---|---|---|---|
| 1262 | >Q4HNM5\|Q4HNM5_CAMUP | *Campylobacter upsaliensis* RM3195. | Thioredoxin PTM_Met 11136.76 | 61.54 | 3.0E−21 |

TABLE 1D-continued

| In Silico ID | Identifier | Sample Name | Protein | USDA Score-β | P-value |
|---|---|---|---|---|---|
| 143 | >A7A905\|A7A905_BIFAD | *Bifidobacterium adolescentis* L2-32. | Putative uncharacterized protein 11134.94 | 25.00 | 9.0E−5 |
| 942 | >A8LX75\|A8LX75_SALAI | *Salinira arenicola* (strain CNS-205). | Putative uncharacterized protein PTM_Met 11140.56 | | |
| 136 | >A6QD71\|A6QD71_STAAE | *Staphylococcus aureus* (strain Newman). | Putative uncharacterized protein 11138.98 | 23.08 | 9.4E−5 |
| 143 | >A7A905\|A7A905_BIFAD | *Bifidobacterium adolescentis* L2-32. | Putative uncharacterized protein 11134.94 | | |
| 145 | >A7BQP4\|A7BQP4_9GAMM | *Beggiatoa* PS. | Putative uncharacterized protein 11132.6 | 23.08 | 1.5E−4 |
| 136 | >A6QD71\|A6QD71_STAAE | *Staphylococcus aureus* (strain Newman). | Putative uncharacterized protein 11138.98 | | |
| 271 | >B1BI09\|B1BI09_CLOPE | *Clostridium perfringens* C str. JGS1495. | Putative uncharacterized protein 11140.05 | 23.08 | 1.5E−4 |
| 449 | >Q2G1R1\|Q2G1R1_STAA8 | *Staphylococcus aureus* (strain NCTC 8325). | Putative uncharacterized protein 11138.98 | | |

MS/MS to In silico Comparison Parameters
Intensity threshold: 2%
m/z range for comparison: 0-14,000 Th.
Fragment ion tolerance: 2.5 Th.
Protein MW 11138 ± 10 Da.
D,E,P-specific in silico fragment ions compared.
"PTM_Met" indicates that the in silico protein sequence was modified to remove the N-terminal methionine.
"PTM_#SigPep" indicates that the in silico protein sequence was modified to remove a signal peptide.
Algorithm computation speeds
USDA peak matching algorithm beta: 18.1 seconds.
P-value calculation: 39.4 seconds.

Table 2A (below) displays the top five identifications of a protein biomarker of *Campylobacter upsaliensis* (strain RM3195) at m/z 12855.3 (as shown in FIG. 4) and analyzed by MS/MS using MALDI-TOF-TOF mass spectrometry and compared to ALL in silico MS/MS fragment ions of bacterial protein sequences having the same molecular weight as the biomarker (within ±5 Da). This corresponded to 1315 in silico protein sequences. The protein biomarker had been identified previously by "bottom-up" proteomics techniques as ribosomal protein 50S L7/L12 (Fagerquist, C. K., 2007, *J. Proteome Res.*, 6, 2539-2549). The top identification correctly identifies the protein biomarker and its source microorganism.

Table 2B (below) displays the top five identifications of a protein biomarker of *Campylobacter upsaliensis* (strain RM3195) at m/z 12855.3 (as shown in FIG. 4) and analyzed by MS/MS using MALDI-TOF-TOF mass spectrometry and compared to D,E,P-specific in silico MS/MS fragment ions of bacterial protein sequences having the same molecular weight as the biomarker (within ±5 Da). This corresponded to 1315 in silico protein sequences. The protein biomarker had been identified previously by "bottom-up" proteomics techniques as ribosomal protein 50S L7/L12 (Fagerquist, C. K., 2007, *J. Proteome Res.*, 6, 2539-2549). The top identification correctly identifies the protein biomarker and its source microorganism.

TABLE 2A

| In Silico ID | Identifier | Sample Name | Protein | USDA Score-α | P-value |
|---|---|---|---|---|---|
| 8942 | >Q4HS60\|Q4HS60_CAMUP | *Campylobacter upsaliensis* RM3195. | Ribosomal protein L7/L12 PTM_Met 12855.65 | 9.32 | 1.1E−10 |
| 8941 | >Q4HDZ9\|Q4HDZ9_CAMCO | *Campylobacter coli* RM2228. | Ribosomal protein L7/L12 PTM_Met 12853.74 | 7.30 | 1.5E−5 |
| 8543 | >A5ZFY2\|A5ZFY2_9BACE | *Bacteroides caccae* ATCC 43185. | Putative uncharacterized protein PTM_Met, 12852.15 | 6.54 | 8.7E−4 |
| 8759 | >B2HXJ0\|B2HXJ0_ACIBA | *Acinetobacter baumannii* ACICU. | Putative transcriptional regulator, TetR family, PTM_Met 12853.04 | 6.30 | 2.8E−3 |
| 8923 | >Q3VUB8\|Q3VUB8_PROAE | *Prosthecochloris aestuarii* DSM 271. | Ribosomal protein L7/L12 PTM_Met 12855.76 | 6.00 | 2.8E−3 |

MS/MS to In silico Comparison Parameters
Intensity threshold: 2%
m/z range for comparison: 0-14,000 Th.
Fragment ion tolerance: 2.5 Th.
Protein MW 12854 ± 10 Da.
ALL in silico fragment ions compared.
"PTM_Met" indicates that the in silico protein sequence was modified to remove the N-terminal methionine.
"PTM_#SigPep" indicates that the in silico protein sequence was modified to remove a signal peptide.
Algorithm Computation Speeds
USDA peak matching algorithm alpha: 34.7 seconds.
P-value calculation: 50.3 seconds.

TABLE 2B

| In Silico ID | Identifier | Sample Name | Protein | USDA Score-α | P-value |
|---|---|---|---|---|---|
| 8942 | >Q4HS60|Q4HS60_CAMUP | Campylobacter upsaliensis RM3195. | Ribosomal protein L7/L12 PTM_Met 12855.65 | 17.75 | 1.3E−15 |
| 8941 | >Q4HDZ9|Q4HDZ9_CAMCO | Campylobacter coli RM2228. | Ribosomal protein L7/L12 PTM_Met 12853.74 | 13.02 | 1.4E−8 |
| 8067 | >B0ACQ4|B0ACQ4_9CLOT | Clostridium bartlettii DSM 16795. | Putative uncharacterized protein 12849.21 | 9.09 | 1.5E−3 |
| 8983 | >Q63UK3|Q63UK3_BURPS | Burkholderia pseudomallei (Pseudomonas pseudomallei). | Putative membrane protein PTM_Met 12847.95 | 8.28 | 2.8E−3 |
| 8008 | >A0HKV3|A0HKV3_COMTE | Comamonas testosteroni KF_1. | Iron_sulfur cluster assembly accessory protein 12856.3 | 8.09 | 4.6E−3 |

MS/MS to In silico Comparison Parameters
Intensity threshold: 2%
m/z range for comparison: 0-14,000 Th.
Fragment ion tolerance: 2.5 Th.
Protein MW 12854 ± 10 Da.
D,E,P-specific in silico fragment ions compared.
"PTM_Met" indicates that the in silico protein sequence was modified to remove the N-terminal methionine.
"PTM_#SigPep" indicates that the in silico protein sequence was modified to remove a signal peptide.
Algorithm Computation Speeds
USDA peak matching algorithm alpha: 16.5 seconds.
P-value calculation: 41.2 seconds.

Table 3A (below) displays the top five identifications of a protein biomarker of *Campylobacter upsaliensis* (strain RM3195) at m/z 9298.3 (as shown in FIG. 4) and analyzed by MS/MS using MALDI-TOF-TOF mass spectrometry and compared to all in silico MS/MS fragment ions of bacterial protein sequences having the same molecular weight as the biomarker (within ±5 Da). This corresponded to 1404 in silico protein sequences. The protein biomarker had been identified previously by "bottom-up" proteomics techniques as 10 kD chaperonin (Fagerquist, C. K., 2007, *J. Proteome Res.*, 6, 2539-2549). The top identification correctly identifies the protein biomarker and its source microorganism.

Table 3B (below) displays the top five identifications of a protein biomarker of *Campylobacter upsaliensis* (strain RM3195) at m/z 9298.3 (as shown in FIG. 4) and analyzed by MS/MS using MALDI-TOF-TOF mass spectrometry and compared to D,E,P-specific in silico MS/MS fragment ions of bacterial protein sequences having the same molecular weight as the biomarker (within ±5 Da). This corresponded to 1404 in silico protein sequences. The protein biomarker had been identified previously by "bottom-up" proteomics techniques as 10 kD chaperonin (Fagerquist, C. K., 2007, *J. Proteome Res.*, 6, 2539-2549). The top identification correctly identifies the protein biomarker and its source microorganism.

TABLE 3A

| In Silico ID | Identifier | Sample Name | Protein | USDA Score-α | P-value |
|---|---|---|---|---|---|
| 10519 | >Q4HRH0|Q4HRH0_CAMUP | Campylobacter upsaliensis RM3195. | Chaperonin, 10 kDa 9299.82 | 15.28 | 3.7E−10 |
| 9741 | >B2JW66|B2JW66_9BURK | Burkholderia phymatum STM815. | PAAR repead_containing protein 9296.43 | 10.68 | 7.1E−4 |
| 9886 | >Q7U8T4|Q7U8T4_SYNPX | Synechococcus (strain WH8102). | Putative uncharacterized protein 9294.61 | 10.97 | 9.0E−4 |
| 9141 | >A4BQR2|A4BQR2_9GAMM | Nitrococcus mobilis Nb_231. | SirA like protein 9296.79 | 10.49 | 3.0E−3 |
| 10507 | >A2P9Y8|A2P9Y8_VIBCH | Vibrio cholerae 1587. | Putative uncharacterized protein PTM_Met 9294.56 | 10.38 | 3.5E−3 |

MS/MS to In silico Comparison Parameters
Intensity threshold: 2%
m/z range for comparison: 0-14,000 Th.
Fragment ion tolerance: 2.5 Th.
Protein MW 9297 ± 10 Da.
All in silico fragment ions compared.
"PTM_Met" indicates that the in silico protein sequence was modified to remove the N-terminal methionine.
"PTM_#SigPep" indicates that the in silico protein sequence was modified to remove a signal peptide.
Algorithm Computation Speeds
USDA peak matching algorithm alpha: 37.9 seconds.
P-value calculation: 80.8 seconds.

TABLE 3B

| In Silico ID | Identifier | Sample Name | Protein | USDA Score-α | P-value |
|---|---|---|---|---|---|
| 10519 | >Q4HRH0\|Q4HRH0_CAMUP | Campylobacter upsaliensis RM3195. | Chaperonin, 10 kDa 9299.82 | 26.88 | 9.3E−16 |
| 10272 | >Q2JWH0\|Q2JWH0_SYNJA | Synechococcus (strain JA_3_3Ab) (Cyanobacteria bacterium Yellowstone A_Prime). | Putative uncharacterized protein PTM_Met 9293.46 | 12.78 | 7.1E−4 |
| 9290 | >A8S0J6\|A8S0J6_9CLOT | Clostridium bolteae ATCC BAA_613. | Putative uncharacterized protein 9301.58 | 11.62 | 5.5E−3 |
| 9445 | >B1UDC6\|B1UDC6_SYNP8 | Synechococcus (strain PCC 8801/RF_1) (Cyanothece PCC 8801). | Putative uncharacterized protein 9299.41 | 11.08 | 6.5E−3 |
| 10361 | >Q5FIU9\|Q5FIU9_LACAC | Lactobacillus acidophilus. | Putative phosphoribosylformylglycinamidine PTM_Met 9293.55 | 11.34 | 7.4E−3 |

MS/MS to In silico Comparison Parameters:
Intensity threshold: 2%.
m/z range for comparison: 0-14,000 Th.
Fragment ion tolerance: 2.5 Th.
Protein MW 9297 ± 10 Da.
D,E,P-specific in silico fragment ions compared.
"PTM_Met" indicates that the in silico protein sequence was modified to remove the N-terminal methionine.
"PTM_#SigPep" indicates that the in silico protein sequence was modified to remove a signal peptide.
Algorithm Computation Speeds
USDA peak matching algorithm alpha: 17.0 seconds.
P-value calculation: 89.7 seconds.

Example 6

The following Example illustrates a "top-down" proteomic approach for protein/microorganism identification of food-borne pathogens. In particular the Example illustrates the identification of a protein biomarker (putative uncharacterized protein yahO) whose amino acid sequence is unique to E. coli O157:H7 strains and thus can be used to distinguish O157:H7 strains from non-O157:H7 strains. Further, the Example illustrates that if multiple microorganisms are present in a culture, it is possible to identify multiple microorganisms on the basis of identification of at least one unique protein biomarker from each microorganism. Indeed, even though a non-genomically sequenced bacterial strain may have extensive protein sequence homology to a closely-related genomically sequenced bacterial strain the bacterial strains may nonetheless have slight differences in protein amino acid sequence. These amino acid variations can change the overall MW of the protein as well as affect the m/z of fragment ions generated from protein fragmentation.

Materials and Methods

Origin and Cultivation of E. coli Strains

E. coli strains were preserved at −80° C. in Microbank™ Microbial Preservation System beads (Pro-Lab Diagnostics, Richmond Hill, Ontario, Canada). The strains were propagated using a bead and streaking for isolation on LB agar (Becton Dickinson, Sparks Md.). The inoculated agar plates were incubated overnight at 37° C. in normal atmosphere. Three E. coli strains were used in this study: two O157:H7 strains (EDL-933 and a Salinas strain) and one non-O157:H7, non-pathogenic E. coli strain. The genomically sequenced strain E. coli O157:H7 strain EDL-933 (designated RM1272 in our strain collection) was originally isolated from raw hamburger associated with hemorrhagic colitis outbreak and binds to anti-O157 and anti-H7 MAbs. The EDL-933 strain was generously provided by Jim Keen, Clay Center, Nebraska. The other O157:H7 strain (designated RM5603 in our strain collection) was isolated from a water sample taken from the Salinas River (Salinas, Calif.) in 2006.

RM5603 is a negative for shiga toxin 1, positive for shiga toxin 2, positive for the intimin gene (eae) and highly positive by PCR. In addition, RM5603 was analyzed by multi-locus variable-number tandem repeat analysis (MLVA). The non-pathogenic E. coli strain RM3061 was isolated from Romaine lettuce as part of a USDA microbiological survey of produce conducted in 2002. This sample was analyzed by Biolog microbial ID (Hayward, Calif.) and identified as a non-pathogenic E. coli.

Protein Biomarker Extraction and Analysis

Bacterial cells were harvested and their proteins extracted as described in detail previously. Briefly, a 1 μL loop of bacterial cells were bead-beat for 1 minute in 0.5 mL of extraction solution (67% water, 33% acetonitrile and 0.1% TFA) with 40 mg of 0.1 mm zirconia/silica beads (BioSpec Products Inc., Bartlesville, Okla.). After bead-beating, the sample was centrifuged at 10,000 rpm for 5 minutes.

MALDI-TOF-TOF-MS Analysis

Cell lysate/protein extract samples were analyzed using a 4800 TOF-TOF™ proteomics analyzer (Applied Biosystems, Foster City, Calif.) as described in detail in a previous report. Briefly, equal aliquot volumes of sample extraction supernatant and a saturated solution of MALDI matrix were mixed. A 0.5 μL aliquot of this mixture was deposited onto a stainless steel target having 384 target spots. Two MALDI matrices were utilized for this study: 3,5-dimethoxy-4-hydroxycinnamic acid (sinapinic acid, $M_r$=224.21 Da) and α-cyano-4-hydroxycinnamic acid (HCCA, $M_r$=189.17 Da). The mass spectrometer is equipped with a pulsed solid-state YAG laser (repetition rate: 200 Hz, λ=355 nm, pulse width: 5 nsec). Samples were analyzed in both linear (MS analysis) and reflectron-modes (MS/MS analysis). The instrument was operated for detection of only positively charged ions. The instrument was externally calibrated in linear mode using bovine insulin (MW=5733.58 Da), E. coli thioredoxin (MW=11673.47 Da) and horse heart apomyoglobin (MW=16,951.55 Da). The instrument was externally calibrated in reflectron-mode using the y-type fragment ions of glu$^1$-fibrino-peptide B (MW=1570.60) at m/z 175.120 and 1441.635.

For MS analysis, laser desorbed ions were accelerated from the source at 20 kV after delayed ion extraction for improved ion focussing. Ions were separated over an effective field free length of 1.5 m before striking a multichannel plate detector operated at 2.190 kV. For MS/MS analysis, ions were accelerated from the source at 8.0 kV after delayed extraction. Ions were separated in a field free region between the source and the collision cell. A timed ion selector (TIS) before the collision cell deflects (mass-selects) ions on the basis of arrival time so that only ions with a pre-selected m/z (i.e. arrival time) pass through the TIS. The TIS window was typically operated at ±100 Da for MS/MS analysis. Ions passing through the TIS were decelerated to 1.70 kV prior to entry into a floating collision cell at 2.0 kV. Ions were fragmented by post-source dissociation (PSD) at higher than normal laser fluence. Ions exiting the collision cell were re-accelerated to 15 kV. An ion gate, after the second acceleration region, was used to suppress the un-fragmented protein ion signal. A two-stage reflectron mirror assembly (mirror 1: 10.910 kV, mirror 2: 18.750 kV) separates and deflects the fragment ions toward the reflectron multichannel plate detector also operated at 2.190 kV.

MS data was collected and summed from 1000-2000 laser shots which provided excellent signal-to-noise (S/N). For MS/MS data, because of low the fragmentation efficiency of singly charged protein ions, 30,000 to 40,000 laser shots were collected and summed in order to improve S/N. At 200 Hz laser repetition rate this required 2-3 minutes data acquisition from a single spot. The ultrafast MALDI target rastering allowed higher than normal laser fluence, required for protein ion fragmentation by PSD, without exhausting the sample spot.

Raw MS and MS/MS data were processed using the instrument software (Data Explorer® Software, Version 4.9). MS data were subjected to noise filtering (correlation factor=0.7). Raw MS/MS data were subjected to an advanced baseline correction (peak width=32, flexibility=0.5, degree=0.1) followed by noise removal (std. dev.=2) followed by a Gaussian smooth (filter width=31 points). Processed MS and MS/MS spectra were centroided and exported as an ASCII file (m/z vs. absolute intensity). MS and MS/MS ASCII files were uploaded to their respective databases in the USDA software.

Results

E. coli O157:H7 Strain EDL-933

Figure 11:
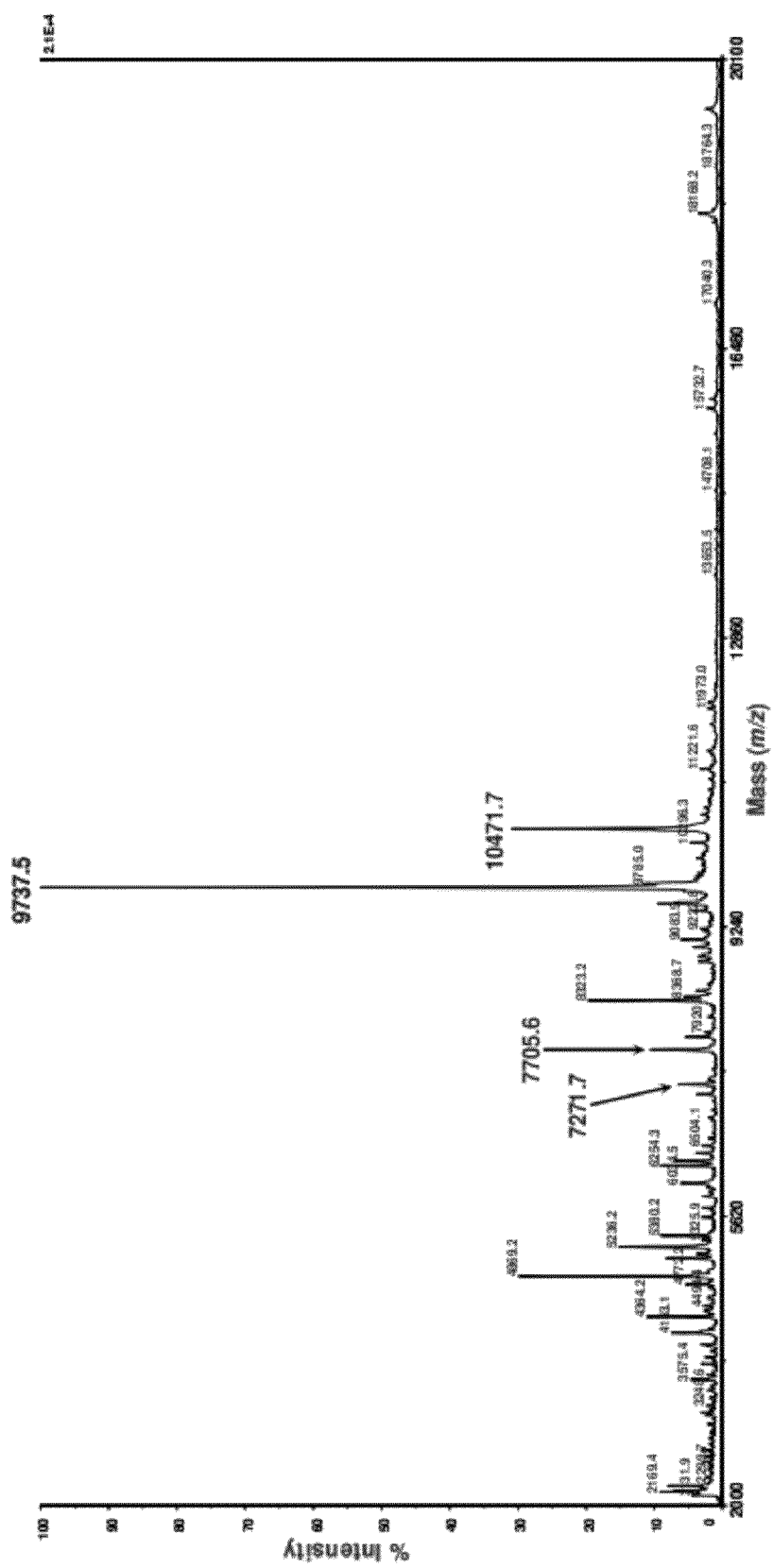
FIG. 11 An MS spectrum of the extracted cell lysate of *E. coli* O157:H7 strain EDL-933 analyzed on the MALDI-TOF-TOF-MS instrument (in linear mode) using HCCA matrix. Data acquisition: 1000 laser shots.

FIG. 11 shows the spectrum from MALDI-TOF-TOF-MS analysis of the extracted cell lysate of E. coli O157:H7 strain EDL-933 (genomically sequenced by Perna and coworkers in 2001, Perna, N. T. et al. (2001) Nature. 409(6819):529-533). The MS data was collected in linear mode with HCCA MALDI matrix.

Figure 12:
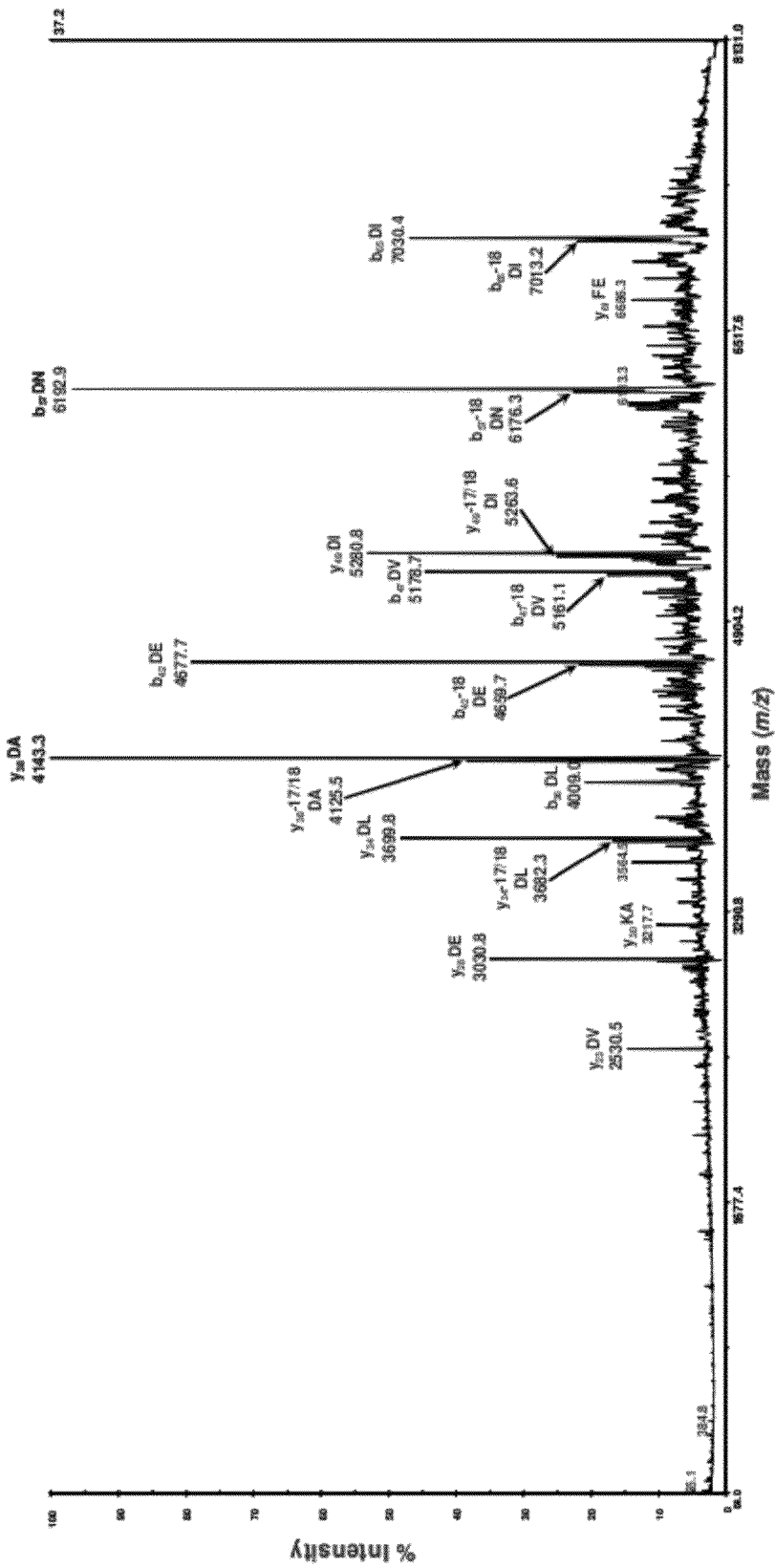
FIG. 12 An MS/MS spectrum of the protein biomarker ion [M+H]$^+$ at m/z 7705.6 (FIG. 11) from *E. coli* O157:H7 strain EDL-933 analyzed on the MALDI-TOF-TOF-MS instrument using HCCA matrix. Data acquisition: 32,000 laser shots. Fragmentation by post-source dissociation (PSD). Prominent fragment ions are identified by their m/z and ion type/number and amino acid residues adjacent to the site of polypeptide backbone cleavage for the amino acid sequence of the top identification: putative uncharacterized protein yahO from *E. coli* O157:H7 strain EDL-933 (Table 4). Many of the fragment ions are the result of a polypeptide cleavage site adjacent to an aspartic acid (D) or glutamic acid (E) residues. The MS/MS data was centroided, exported as an ASCII formatted file and uploaded to the USDA software for analysis.

FIG. 12 shows the MS/MS spectrum, as viewed in the instrument software, of the protein biomarker ion a m/z 7705.6 shown in FIG. 11. Prominent fragment ions are identified by their m/z and ion type/number and amino acid residues adjacent to the site of polypeptide backbone cleavage for the protein amino acid sequence of the top identification shown in Table 4: putative uncharacterized protein yahO of the pathogenic E. coli O157:H7 strain EDL-933. As can be seen, many of the fragment ions are the result of polypeptide cleavage adjacent to aspartic (D) and/or glutamic acid (E) residues. The MS/MS data in FIG. 12 was centroided, exported from the instrument software as an ASCII formatted file (m/z vs. absolute intensity) and uploaded to the USDA software for analysis.

Table 4 (below) shows the top five identifications of the protein biomarker of E. coli O157:H7 strain EDL-933 at m/z 7705.6 (shown in FIG. 11) and analyzed by MS/MS using MALDI-TOF-TOF mass spectrometry and compared to all in silico fragment ions of bacterial protein sequences having the same MW as the biomarker within a tolerance of ±5 Da. The top identification of both the USDA peak matching algorithm β and the p-value calculation correctly identified the source microorganism. The protein biomarker was identified as the putative uncharacterized protein yahO. The scores of the 1st and 2nd identification are significantly different compared to the other runner-up identifications. This is reflective of the very high quality of this MS/MS spectrum. In addition, it was possible to distinguish between the pathogenic E. coli O157: H7 strain EDL-933 and the non-pathogenic E. coli strain K-12 with this protein biomarker. As can be seen, the USDA peak matching algorithm β was approximately three times faster than the p-value calculation in terms of computation speed.

TABLE 4

| In Silico ID | Identifier | Sample Name | Protein | USDA Score-β | P-value |
|---|---|---|---|---|---|
| 26947 | >tr\|Q8X699\|Q8X699_ECO57 | Escherichia coli O157:H7 (strain EDL-933) | Putative uncharacterized protein yahO (Putative uncharacterized protein ECs0383) PTM-21SigPep 7707.62 | 66.30 | 4.3E−18 |
| 26281 | >sp\|P75694\|YAHO_ECOLI | Escherichia coli (strain K-12) | UPF0379 protein yahO PTM-21SigPep 7706.64 | 63.04 | 9.0E−16 |
| 25925 | tr\|B3G283\|B3G283_PSEAE | Pseudomonas aeruginosa | Putative uncharacterized protein 7709.01 | 44.57 | 4.8E−5 |
| 25880 | >tr\|B1SUG8\|B1SUG8_9BACI | Geobacillus WCH70 | Putative uncharacterized protein 7707.91 | 38.04 | 4.9E−4 |

TABLE 4-continued

| In Silico ID | Identifier | Sample Name | Protein | USDA Score-β | P-value |
|---|---|---|---|---|---|
| 26056 | >tr|Q20ZY6|Q20ZY6_RHOPB | Rhodopseudomonas palustris (strain BisB18) | Rubredoxin type Fe(Cys)4 protein 7695.44 | 38.04 | 1.3E−3 |

MS/MS to in silico comparison parameters
Intensity threshold: 2%
Number of MS/MS peaks with intensity ≧2%: 92.
m/z range for comparison: 0-14,000 Th.
Fragment ion tolerance: 2.5 Th.
Protein MW 7705 ± 10 Da. Number of bacterial proteins 1320.
All in silico fragment ions compared.
"PTM N-Met" indicates that the in silico protein sequence was modified to remove the N-terminal methionine.
"PTM #SigPep" indicates that the in silico protein sequence was modified to remove a signal peptide.
Algorithm computation times
USDA peak matching algorithm beta: 35.7 seconds.
P-value: 101.0 seconds.

FIG. 13 shows the primary amino acid sequence of the putative uncharacterized protein yahO of the pathogenic *E. coli* O157:H7 strain EDL-933 strain (SEQ ID NO:1) and the UPF0379 protein yahO of the non-pathogenic *E. coli* strain K-12 strain (SEQ ID NO:2). Both proteins have a 21 residue N-terminal signal peptide (boxed). The two proteins are different by two amino acid substitutions. A F↔L substitution at residue in the signal peptide and a D↔N substitution that results in a protein MW difference of 1 Da in the mature protein. Such slight differences in protein biomarker MW are difficult to detect by MALDI-TOF-MS, however sequence-specific fragmentation by MS/MS allows these two proteins (and their source microorganisms) to be differentiated.

Identification of the putative uncharacterized protein yahO of *E. coli* O157:H7 strain EDL-933 was facilitated due to the high sequence homology to UPF0379 protein yahO of *E. coli* strain K-12. The putative uncharacterized protein yahO of *E. coli* O157:H7 strain EDL-933 currently in Expasy databases (>tr|Q8X699|Q8x699_ECO57) is displayed as the unprocessed protein sequence with no indication that this protein might possess a signal peptide. In consequence, this protein was not retrieved during the initial TagIdent protein MW search. However, the search did retrieve UPF0379 protein yahO of *E. coli* K-12 (>sp|P75694|YAHO_ECOLI) which possessed a 21-residue N-terminal signal peptide. The signal peptide-containing yahO sequence of *E. coli* K-12 (and other signal-peptide containing proteins) was identified from its larger file size. The signal peptides were removed from the in silico sequences, processed and uploaded by methods known in the art. Initially, the top identification of MS/MS of the m/z 7705.6 biomarker ion (FIG. 12) of *E. coli* O157:H7 strain EDL-933 was UPF0379 protein yahO of *E. coli* strain K-12 with a 21-residue N-terminal signal peptide and no other "runner up" identifications of *E. coli* among the top 5 identifications. Working on the assumption that the Expasy database may not indicate that yahO protein of *E. coli* O157:H7 strain EDL-933 possessed a signal peptide, a targeted search was conducted for the yahO protein and *E. coli* O157:H7 strain EDL-933 which resulted in the identification of an unprocessed sequence of putative uncharacterized protein yahO *E. coli* O157:H7 strain EDL-933. This sequence was processed to remove twenty-one residues from the N-terminus. The FastA file was then processed by methods known in the art and uploaded to the USDA software that in this instance utilized the USDA peak matching algorithm β. The MS/MS data was re-analyzed and the results are displayed in Table 4. Further inspection of Expasy database revealed nine other strains of *E. coli* O157:H7 whose yahO unprocessed sequence is identical to the yahO sequence of strain EDL-933. They are: EC4196, EC4113, EC4076, EC4401, EC4486, EC4501, EC869, EC508 and EC4115/EHEC. Thus, it would not be possible to distinguish between different strains of *E. coli* O157:H7 using only the yahO protein biomarker.

Although there is only a one residue difference (N↔D) between the amino acid sequences of the mature yahO protein of *E. coli* strain K-12 and *E. coli* O157:H7 strain EDL-933 (SEQ ID NO:1) (FIG. 13), this difference involves an aspartic acid residue substitution. Aspartic acid residues facilitate fragmentation of singly protonated protein ions. Without being bound by theory it is believed that fragmentation is facilitated because the short acidic side chain allows transfer of its acidic proton to the polypeptide backbone thereby increasing the fragmentation efficiency of the polypeptide backbone. The other consequence of the N↔D substitution is that the difference in mass of the mature yahO proteins is only 1 Da. Such slight differences in protein biomarker MW are nearly impossible to detect by MALDI-TOF-MS, however sequence-specific fragmentation by MS/MS allows these two yahO proteins (and their source microorganisms) to be differentiated.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for identification of an unknown protein, the method comprising:
   (i) extracting the unknown protein from a sample;
   (ii) preparing the unknown protein for laser desorption/ionization mass spectrometry;
   (iii) using the mass spectrometer to ionize and fragment the unknown protein, thereby performing a chemical analysis and obtaining a mass spectrum of the unknown protein;
   (iv) comparing mass-to-charge (m/z) fragment ion peaks from the mass spectrum of the unknown protein to that of m/z fragment ion peaks from mass spectra of known protein sequences; and
   (v) matching the m/z fragment ion peaks from the mass spectrum of the unknown protein to the m/z fragment ion peaks from the mass spectra of known protein sequences to provide mass spectrometry peak matches;
   (vi) scoring the mass spectrometry peak matches using a USDA peak matching algorithm thereby providing a USDA peak matching score; and
   (vii) ranking the USDA peak matching score from highest to lowest;
   wherein
   the highest USDA peak matching score constitutes an identification of the unknown protein.

2. The method of claim 1, wherein the USDA peak matching algorithm is USDA peak matching algorithm α, which has the formula:

$$\text{USDA}\alpha \text{ Score} = 100 \times \frac{2 \times (\text{Number of peak matches})}{(\text{Number of peaks in the mass spectrum of the unknown protein} + \text{Number of peaks in the mass spectrum of known protein sequences})}.$$

3. The method of claim 1, wherein the USDA peak matching algorithm is USDA peak matching algorithm β, which has the formula:

$$\text{USDA}\beta \text{ Score} = 100 \times \frac{\text{Number of peak matches}}{(\text{Number of } MS/MS \text{ fragment ion peaks})}.$$

wherein the MS/MS fragment ion peaks are peaks on an intensity vs m/z (mass to charge ratio) plot of fragment ions having an intensity above a specified threshold, which are generated by tandem mass spectrometry of an unknown protein.

4. The method of claim 1, wherein a difference between the highest USDA peak matching score and a second highest USDA peak matching score is calculated, and the difference is equal to or greater than 2.

5. The method of claim 1, wherein the mass spectra are members selected from the group consisting of a mass spectrum produced by a mass spectrometer having a single mass analyser (MS spectrum) and a mass spectrum produced by a tandem mass spectrometer (MS/MS spectrum).

6. The method of claim 5, wherein the mass spectrum of the unknown protein is an MS spectrum and wherein the mass spectra of known protein sequences are MS spectra of known proteins.

7. The method of claim 5, wherein the mass spectrum of the unknown protein is an MS/MS spectrum and wherein the mass spectra of known protein sequences are members of the group consisting of in silico MS/MS spectra generated from a genomically-derived database of protein sequences and MS/MS spectra of known proteins.

8. The method of claim 7, wherein the mass spectra of known protein sequences are in silico MS/MS spectra generated from a genomically-derived database of protein sequences.

9. The method of claim 8, further comprising:
(v) confirming that the highest USDA peak matching score constitutes an identification of the unknown protein, wherein the confirming comprises:
plotting the difference in m/z ($\Delta$m/z) between an MS/MS fragment ion of the unknown protein and its matched fragment ion from the in silico MS/MS spectra generated from a genomically-derived database of protein sequences as a function of MS/MS fragment ion m/z,
thereby providing a plot of $\Delta$m/z vs MS/MS fragment ion m/z,
wherein
a correct protein identification is indicated when the plot of $\Delta$m/z vs MS/MS fragment ion m/z reveals a characteristic systematic error related to the inherent calibration error of the mass analyzer, and
wherein
an incorrect protein identification is indicated when the plot of $\Delta$m/z vs MS/MS fragment ion m/z reveals statistically random error.

10. The method of claim 8, further comprising:
(v) confirming that the highest USDA peak matching score constitutes an identification of the unknown protein, wherein the confirming comprises:
performing steps (i)-(iv), wherein the in silico MS/MS spectra generated from a genomically-derived database of protein sequences are limited to spectra generated by displaying only fragment ions generated by fragmentation at an aspartate (D) residue, glutamate (E) residue or proline (P) residue, and
(vi) observing that the difference between the highest USDA peak matching score and the second highest USDA peak matching score is equal to or greater than the difference between the highest USDA peak matching score and the second highest USDA peak matching score obtained when steps (i)-(iv) are performed using in silico MS/MS spectra generated from a genomically-derived database of protein sequences that are not limited spectra generated by displaying only fragment ions generated by fragmentation at an aspartate (D) residue, glutamate (E) residue or proline (P) residue,
thereby confirming that the highest USDA peak matching score constitutes an identification of the unknown protein.

11. The method of claim 10, wherein the confirming comprises:
performing steps (i)-(iv), wherein the in silico MS/MS spectra generated from a genomically-derived database of protein sequences are limited to spectra generated by displaying only fragment ions generated by fragmentation at an aspartate (D) residue; and
(vi) observing that the difference between the highest USDA peak matching score and the second highest USDA peak matching score is equal to or greater than the difference between the highest USDA peak matching score and the second highest USDA peak matching score obtained when steps (i)-(iv) are performed using in silico MS/MS spectra generated from a genomically-derived database of protein sequences that are not limited spectra generated by displaying only fragment ions generated by fragmentation at an aspartate (D) residue,
thereby confirming that the highest USDA peak matching score constitutes an identification of the unknown protein.

12. The method of claim 1, wherein the unknown protein is a protein toxin.

13. The method of claim 1, wherein identification of the unknown protein is used to identify the source organism from which the unknown protein derived.

14. The method of claim 13, wherein the source organism is a member selected from the group consisting of: viruses, microorganisms, insects, plants, and animals.

15. The method of claim 13, wherein the source organism is a microorganism selected from the group consisting of: bacteria and fungi.

16. The method of claim 15, wherein the source organism is a bacterium that is a member selected from the group consisting of *Campylobacter, Escherichia coli, Listeria*, and *Salmonella*.

17. A non-transitory computer readable medium containing computer instructions stored therein for causing a computer processor to perform a method for identification of an unknown protein comprising:
(i) comparing mass-to-charge (m/z) fragment ion peaks from an mass spectrum of the unknown protein to that of m/z fragment ion peaks from mass spectra of known protein sequences; and
(ii) matching the m/z fragment ion peaks from the mass spectrum of the unknown protein to the m/z fragment ion peaks from the mass spectra of known protein sequences to provide mass spectrometry peak matches;
(iii) scoring the mass spectrometry peak matches using a USDA peak matching algorithm thereby providing a USDA peak matching score; and
(iv) ranking the USDA peak matching score from highest to lowest;
wherein
the highest USDA peak matching score constitutes an identification of the unknown protein.

18. The method of claim 17, wherein the USDA peak matching algorithm is USDA peak matching algorithm $\alpha$, which has the formula:

$$\text{USDA}\alpha \text{ Score} = 100 \times \frac{2 \times (\text{Number of peak matches})}{(\text{Number of peaks in the mass spectrum of the unknown protein} + \text{Number of peaks in the mass spectrum of known protein sequences})}.$$

19. The method of claim 17, wherein the USDA peak matching algorithm is USDA peak matching algorithm $\beta$, which has the formula:

$$\text{USDA}\beta \text{ Score} = 100 \times \frac{\text{Number of peak matches}}{(\text{Number of MS/MS fragment ion peaks})}.$$

wherein the MS/MS fragment ion peaks are peaks on an intensity vs m/z (mass to charge ratio) plot of fragment ions having an intensity above a specified threshold, which are generated by tandem mass spectrometry of an unknown protein.

20. The method of claim 17, wherein a difference between the highest USDA peak matching score and the second highest USDA peak matching score is calculated and the difference is equal to or greater than 2.

21. The method of claim 17, wherein the mass spectra are members selected from the group consisting of a mass spectrum produced by a mass spectrometer having a single mass analyser (MS spectrum) and a mass spectrum produced by a tandem mass spectrometer (MS/MS spectrum).

22. The method of claim 21, wherein the mass spectrum of the unknown protein is an MS spectrum and wherein the mass spectra of known protein sequences are MS spectra of known proteins.

23. The method of claim 21, wherein the mass spectrum of the unknown protein is an MS/MS spectrum and wherein the mass spectra of known protein sequences are members of the group consisting of in silico MS/MS spectra generated from a genomically-derived database of protein sequences and MS/MS spectra of known proteins.

24. The method of claim 23, wherein the mass spectra of known protein sequences are in silico MS/MS spectra generated from a genomically-derived database of protein sequences.

25. The method of claim 24, further comprising:
(v) confirming that the highest USDA peak matching score constitutes an identification of the unknown protein,
wherein the confirming comprises:
plotting the difference in m/z ($\Delta$m/z) between an MS/MS fragment ion of the unknown protein and its matched fragment ion from the in silico MS/MS spectra generated from a genomically-derived database of protein sequences as a function of MS/MS fragment ion m/z,
thereby providing a plot of $\Delta$m/z vs MS/MS fragment ion m/z,
wherein
a correct protein identification is indicated when the plot of $\Delta$m/z vs MS/MS fragment ion m/z reveals a characteristic systematic error related to the inherent calibration error of the mass analyzer, and
wherein
an incorrect protein identification is indicated when the plot of $\Delta$m/z vs MS/MS fragment ion m/z reveals statistically random error.

26. The method of claim 24, further comprising:
(v) confirming that the highest USDA peak matching score constitutes an identification of the unknown protein,
wherein the confirming comprises:
performing steps (i)-(iv), wherein the in silico MS/MS spectra generated from a genomically-derived database of protein sequences are limited to spectra generated by displaying only fragment ions generated by fragmentation at an aspartate (D) residue, glutamate (E) residue or proline (P) residue, and
(vi) observing that the difference between the highest USDA peak matching score and the second highest USDA peak matching score is equal to or greater than the difference between the highest USDA peak matching score and the second highest USDA peak matching score obtained when steps (i)-(iv) are performed using in silico MS/MS spectra generated from a genomically-derived database of protein sequences that are not limited spectra generated by displaying only fragment ions generated by fragmentation at an aspartate (D) residue, glutamate (E) residue or proline (P) residue,
thereby that the highest USDA peak matching score constitutes an identification of the unknown protein.

27. The method of claim 26, wherein the confirming comprises:
performing steps (i)-(iv), wherein the in silico MS/MS spectra generated from a genomically-derived database of protein sequences are limited to spectra generated by displaying only fragment ions generated by fragmentation at an aspartate (D) residue; and
(vi) observing that the difference between the highest USDA peak matching score and the second highest USDA peak matching score is equal to or greater than the difference between the highest USDA peak matching score and the second highest USDA peak matching score obtained when steps (i)-(iv) are performed using in silico MS/MS spectra generated from a genomically-derived database of protein sequences that are not limited spectra generated by displaying only fragment ions generated by fragmentation at an aspartate (D) residue,
thereby confirming that the highest USDA peak matching score constitutes an identification of the unknown protein.

28. The method of claim 17, wherein the unknown protein is a protein toxin.

29. The method of claim 17, wherein identification of the unknown protein is used to identify the source organism from which the unknown protein derived.

30. The method of claim 29, wherein the source organism is a member selected from the group consisting of: viruses, microorganisms, insects, plants, and animals.

31. The method of claim 30, wherein the source organism is a microorganism selected from the group consisting of: bacteria and fungi.

32. The method of claim 31, wherein the source organism is a bacterium that is a member selected from the group consisting of *Campylobacter, Escherichia coli, Listeria*, and *Salmonella*.

* * * * *